US008530478B2

(12) United States Patent
Beswick et al.

(10) Patent No.: US 8,530,478 B2
(45) Date of Patent: *Sep. 10, 2013

(54) PIPERAZINE DERIVATIVES USED AS CAV2.2 CALCIUM CHANNEL MODULATORS

(75) Inventors: Paul John Beswick, Harlow (GB); Alister Campbell, Harlow (GB); Andrew Peter Cridland, Harlow (GB); Robert James Gleave, Harlow (GB); Jag Paul Heer, Harlow (GB); Neville Hubert Nicholson, Harlow (GB); Lee William Page, Harlow (GB); Sadie Vile, Harlow (GC)

(73) Assignee: Convergence Pharmaceuticals Limited, London (GB)

(*) Notice: Subject to any disclaimer, the term of this patent is extended or adjusted under 35 U.S.C. 154(b) by 210 days.

This patent is subject to a terminal disclaimer.

(21) Appl. No.: 13/054,265

(22) PCT Filed: Jul. 15, 2009

(86) PCT No.: PCT/EP2009/059011
§ 371 (c)(1),
(2), (4) Date: Jan. 14, 2011

(87) PCT Pub. No.: WO2010/007072
PCT Pub. Date: Jan. 21, 2010

(65) Prior Publication Data
US 2011/0130379 A1      Jun. 2, 2011

(30) Foreign Application Priority Data
Jul. 17, 2008 (GB) .................................. 0813142.7

(51) Int. Cl.
*A61K 31/496* (2006.01)
*C07D 401/06* (2006.01)
(52) U.S. Cl.
USPC ........................... 514/253.13; 544/365
(58) Field of Classification Search
None
See application file for complete search history.

(56) References Cited

U.S. PATENT DOCUMENTS

| | | | |
|---|---|---|---|
| 5,466,823 A | 11/1995 | Talley et al. | |
| 5,474,995 A | 12/1995 | Ducharme et al. | |
| 5,633,272 A | 5/1997 | Talley et al. | |
| 6,291,523 B1 | 9/2001 | Fujimoto et al. | |
| 6,310,099 B1 | 10/2001 | Fujimoto et al. | |
| 8,288,388 B2 * | 10/2012 | Beswick et al. | 514/253.13 |

FOREIGN PATENT DOCUMENTS

| | | |
|---|---|---|
| DE | 10155684 | 5/2003 |
| WO | WO 96/25405 | 8/1996 |
| WO | WO 97/14691 | 4/1997 |
| WO | WO 97/38986 | 10/1997 |
| WO | WO 98/03484 | 1/1998 |
| WO | WO 99/12930 | 3/1999 |
| WO | WO 00/26216 | 5/2000 |
| WO | WO 00/52008 | 9/2000 |
| WO | WO 01/38311 | 5/2001 |
| WO | WO 01/58881 | 8/2001 |
| WO | WO 02/18374 | 3/2002 |
| WO | WO 2007/111921 | 10/2007 |
| WO | 2008/024284 | * 2/2008 |
| WO | WO 2008/024284 | 2/2008 |

OTHER PUBLICATIONS

CA Registry No. 850018-38-1, entered into the Registry File on May 9, 2005, supplied by Enamine.*
CA Registry No. 1012528-09-4, entered into the Registry File on Apr. 6, 2008, supplied by Ambinter.*
CA Registry No. 1099276-21-7, entered into the Registry File on Feb. 2, 2009, supplied by UkroOrgSynthesis.*
CA Registry No. 1099326-83-6, entered into the Registry File on Feb. 2, 2009, supplied by UkroOrgSynthesis.*
Berge, S.M., et al., "Pharmaceutical Salts," *J. Pharm. Sci.*, 66(1): 1-19 (1977).
Bowersox, S.A., et al., "Selective N-Type Neuronal Voltage-Sensitive Calcium Channel Blocker, SNX-111, Produces Spinal Antinociception in Rat Models of Acute, Persistent and Neuropathic Pain," *J. Pharm. and Exper. Therap.*, 279(3): 1243-1249 (1996).
Brose, W.G., et al., "Use of Intrathecal SNX-111, a Novel, N-Type, Voltage-Sensitive, Calcium Channel Blocker, in the Management of Intractable Brachial Plexus Avulsion Pain," *Clin. J. Pain*, 13: 256-259 (1997).
Bundgaard, H., "Design of Prodrugs: Bioreversible Derivatives for Functional Groups and Chemical Entities," *Design of Prodrugs*, 1-49 (1985).
CAS Database Accession No. 1009896-34-7, entered into STN Mar. 25, 2008.
CAS Database Accession No. 461428-49-9, entered into STN Oct. 15, 2002.
CAS Database Accession No. 849191-30-6, entered into STN Apr. 26, 2005.
Ferres, H., "Pro-Drugs of B-Lactam Antibiotics," *Drugs of Today*, 19(9): 499-538 (1983).
Scapecchi, S., et al., "Structure-Activity Relationship Studies on Unifiram (DM232) and Sunifiram (DM235), Two Novel and Potent Cognition Enhancing Drugs," *Bioorganic & Medicinal Chemistry* 12: 71-85 (2004).
Smith, M.T., et al., The Novel N-Type Calcium Channel Blocker, AM336, Produces Potent Dose-Dependent Antinociception After Intrathecal Dosing in Rats and Inhibits Substance P Release in Rat Spinal Cord Slices, *Pain*, 96: 119-127 (2002).
Winquist, R.J., et al., "Use-Dependent Blockade of Cav2.2 Voltage-Gated Calcium Channels for Neuropathic Pain," *Biochemical Pharmacology*, 70: 489-499 (2005).

\* cited by examiner

*Primary Examiner* — Emily Bernhardt
(74) *Attorney, Agent, or Firm* — Womble Carlyle Sandridge & Rice, LLP

(57) ABSTRACT

The present invention relates to novel piperazine derivatives (I); to processes for their preparation; to pharmaceutical compositions containing the derivatives; and to the use of the derivatives in therapy to treat diseases for which blocking the $Ca_v2.2$ calcium channels is beneficial.

25 Claims, No Drawings

PIPERAZINE DERIVATIVES USED AS CAV2.2 CALCIUM CHANNEL MODULATORS

CROSS REFERENCE TO RELATED APPLICATIONS

This application claims priority to PCT Application Number PCT/EP2009/059011, with an International Filing Date of 15 Jul. 2009, and GB Application No. 0813142.7 filed on 17 Jul. 2008, each of which is herein incorporated by reference in its entirety.

The present invention relates to novel piperazine derivatives; to processes for their preparation; to pharmaceutical compositions containing the derivatives; and to the use of the derivatives in therapy to treat diseases for which blocking the $Ca_v2.2$ calcium channels is beneficial.

Pre-synaptic $Ca_v2.2$ (N-type) voltage-gated calcium channels in the dorsal horn of the spinal cord modulate the release of key pro-nociceptive neurotransmitters such as glutamate, substance P (SP) and calcitonin-gene-related peptide (CGRP), indicating the potential therapeutic use of $Ca_v2.2$ calcium channel blockers as analgesics.

Peptidic ω-conotoxins, isolated from the venom of cone snails, have been shown to be selective for $Ca_v2.2$ calcium channels and can block SP release in the spinal cord (Smith et al. (2002) Pain, 96: 119-127). Moreover, they have been shown to be antinociceptive in animal models of chronic pain following intrathecal administration (Bowersox et al. (1996) Journal of Pharmacology and Experimental Therapeutics, 279: 1243-1249; Smith et al. (2002) supra), and have been shown to be effective analgesics in clinical use, particularly in the treatment of neuropathic pain (Brose et al. (1997) Clinical Journal of Pain, 13: 256-259).

In addition, $Ca_v2.2$ calcium channels have been shown to be important for normal neuronal function (Winquist et al. (2005) Biochemical Pharmacology, 70: 489-499). Therefore, the aim is to identify novel molecules that preferentially block $Ca_v2.2$ under conditions of increased neuronal excitability, so-called use-dependent blockers, as is the case in chronic pain syndromes.

WO 2007/111921 (Amgen Inc) describes a series of diaza-heterocyclic amide derivatives which are claimed to be useful in the treatment of diabetes, obesity and related conditions and disorders. DE 10155684 (Bayer AG) describes a series of 2-[[(aminosulfonyl)phenyl]ureido]thiazoles as antibiotics. WO 2008/024284 (Merck & Co) describes a series of sulfonylated piperazines as cannabinoid-1 (CB1) receptor modulators which are claimed to be useful in the treatment for example of psychosis, cognitive disorders and Alzheimer's disease.

The present invention provides compounds which are capable of blocking these $Ca_v2.2$ calcium channels.

In a first aspect there is provided a compound of formula (I), or a pharmaceutically acceptable salt thereof, for use in therapy, wherein:

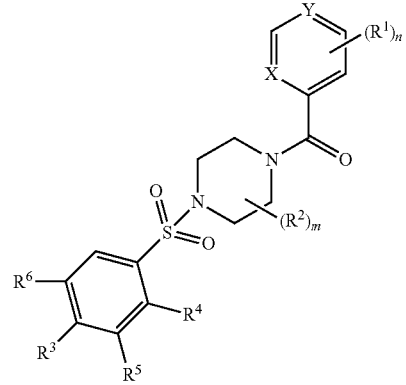

X is nitrogen and Y is carbon, or X is carbon and Y is nitrogen;
m and n are independently selected from 0, 1 and 2;
where present, each $R^1$ is independently selected from $C_{1-4}$ alkyl, $C_{1-4}$ alkoxy, $C_{3-6}$ cycloalkyl, cyano, $NR^{1a}R^{1b}$ and halogen;
$R^{1a}$ and $R^{1b}$ are independently selected from hydrogen, $C_{1-4}$ alkyl, $C_{3-6}$ cycloalkyl and a 4 to 6 membered heterocyclyl; or $R^{1a}$ and $R^{1b}$ together with the nitrogen atom to which they are attached form a 4 to 6 membered heterocyclic ring;
where present, each $R^2$ is $C_{1-4}$ alkyl;
$R^3$ is hydrogen, halogen, cyano, $C_{1-4}$ haloalkyl or $C_{1-4}$ haloalkoxy;
$R^4$ is hydrogen or $C_{1-4}$ alkyl;
$R^5$ is hydrogen, halogen, cyano, $C_{1-4}$ haloalkyl or $C_{1-4}$ haloalkoxy;
$R^6$ is hydrogen, halogen, cyano, $C_{1-4}$ haloalkyl or $C_{1-4}$ haloalkoxy;
such that at least 1 of $R^3$, $R^4$, $R^5$ and $R^6$ is a group other than hydrogen.

In a second aspect there is provided a compound of formula (I), or a salt thereof, wherein
X is nitrogen and Y is carbon, or X is carbon and Y is nitrogen;
m and n are independently selected from 0, 1 and 2;
where present, each $R^i$ is independently selected from $C_{1-4}$ alkyl, $C_{1-4}$ alkoxy, $C_{3-6}$ cycloalkyl, cyano, $NR^{1a}R^{1b}$ and halogen;
$R^{1a}$ and $R^{1b}$ are independently selected from hydrogen, $C_{1-4}$ alkyl, $C_{3-6}$cycloalkyl and a 4 to 6 membered heterocyclyl; or $R^{1a}$ and $R^{1b}$ together with the nitrogen atom to which they are attached form a 4 to 6 membered heterocyclic ring;
where present, each $R^2$ is $C_{1-4}$ alkyl;
$R^3$ is hydrogen, halogen, cyano, $C_{1-4}$ haloalkyl or $C_{1-4}$ haloalkoxy;
$R^4$ is hydrogen or $C_{1-4}$ alkyl;
$R^5$ is hydrogen, halogen, cyano, $C_{1-4}$ haloalkyl or $C_{1-4}$ haloalkoxy;
$R^6$ is hydrogen, halogen, cyano, $C_{1-4}$ haloalkyl or $C_{1-4}$ haloalkoxy;
such that at least 1 of $R^3$, $R^4$, $R^5$ and $R^6$ is a group other than hydrogen;
with the proviso that the compound is not
1-[(4-chlorophenyl)sulfonyl]-4-(2-pyridinylcarbonyl)piperazine;
1-[(4-chlorophenyl)sulfonyl]-4-[(4-chloro-2-pyridinyl)carbonyl]piperazine;
1-[(3-chlorophenyl)sulfonyl]-4-(4-pyridinylcarbonyl)piperazine;
1-[(4-chlorophenyl)sulfonyl]-4-(4-pyridinylcarbonyl)piperazine;

1-{[4-chloro-3-(trifluoromethyl)phenyl]sulfonyl}-4-(2-pyridinylcarbonyl)piperazine;
1-[(4-chloro-2-pyridinyl)carbonyl]-4-{[4-(trifluoromethyl)phenyl]sulfonyl}piperazine;
1-{[4-chloro-3-(trifluoromethyl)phenyl]sulfonyl}-4-(4-pyridinylcarbonyl)piperazine;
1-(4-pyridinylcarbonyl)-4-{[4-(trifluoromethyl)phenyl]sulfonyl}piperazine;
1-(4-pyridinylcarbonyl)-4-{[3-(trifluoromethyl)phenyl]sulfonyl}piperazine;
1-(2-pyridinylcarbonyl)-4-{[3-(trifluoromethyl)phenyl]sulfonyl}piperazine;
1-(2-pyridinylcarbonyl)-4-{[4-(trifluoromethyl)phenyl]sulfonyl}piperazine;
1-(2-pyridinylcarbonyl)-4-({-4-[(trifluoromethy)oxy]phenyl}sulfonyl)piperazine;
1-(4-pyridinylcarbonyl)-4-({-4-[(trifluoromethy)oxy]phenyl}sulfonyl)piperazine; and
1-{[3,5-bis(trifluoromethyl)phenyl]sulfonyl}-4-(4-pyridinylcarbonyl)piperazine.

It is understood that in formula (I), when present, $R^1$ may be attached to any one of the four possible carbon atoms in the pyridyl ring.

As used herein, the term "alkyl" (when used as a group or as part of a group) refers to a straight or branched hydrocarbon chain containing the specified number of carbon atoms. For example, $C_{1-6}$ alkyl means a straight or branched hydrocarbon chain containing at least 1 and at most 6 carbon atoms. Examples of alkyl include, but are not limited to; methyl (Me), ethyl (Et), n-propyl, i-propyl, t-butyl, n-hexyl and i-hexyl.

As used herein, the term "alkoxy" (when used as a group or as part of a group) refers to an —O-alkyl group wherein alkyl is as defined hereinbefore.

The term 'halogen' is used herein to describe, unless otherwise stated, a group selected from fluoro (fluorine), chloro (chlorine), bromo (bromine) or iodo (iodine). In one embodiment, the term 'halogen' is used herein to describe, unless otherwise stated, a group selected from chloro (chlorine) or bromo (bromine).

The term $C_{1-4}$ haloalkyl as used herein refers to a $C_{1-4}$ alkyl group as defined herein substituted with one or more halogen groups, e.g. $CF_3$, $CF_2H$ or $CF_3CH_2$.

The term $C_{1-4}$ haloalkoxy as used herein refers to an $C_{1-4}$ alkoxy group as defined herein substituted with one or more halogen groups, e.g. —O—$CF_3$.

The term $C_{3-6}$ cycloalkyl as used herein refers to a saturated monocyclic hydrocarbon ring of 3 to 6 carbon atoms. Examples of such groups include cyclopropyl, cyclobutyl, cyclopentyl and cyclohexyl.

The term 4 to 6 membered heterocyclic ring and its monovalent radical refers to a 4 to 6 membered saturated monocyclic ring which contains 1 or 2 heteroatoms independently selected from oxygen, nitrogen and sulphur. Suitable examples of such groups include pyrrolidinyl, piperidinyl, piperazinyl, morpholinyl, thiomorpholinyl and azetidinyl.

In one embodiment of the first or second aspect, X is nitrogen and Y is carbon, or X is carbon and Y is nitrogen. In another embodiment of the first or second aspect, X is nitrogen and Y is carbon. In a further embodiment of the first or second aspect, X is carbon and Y is nitrogen.

In one embodiment of the first or second aspect, $R^1$ is selected from $C_{1-4}$ alkyl, $C_{1-4}$ alkoxy, cyano and $NR^{1a}R^{1b}$. In another embodiment of the first or second aspect, $R^1$ is selected from $C_{1-4}$ alkyl and $C_{1-4}$ alkoxy. In one particular embodiment of the first or second aspect, $R^1$ is selected from methyl and methoxy. In a more particular embodiment of the first or second aspect, $R^1$ is selected from 2-methyl, 6-methyl, 2-methoxy and 6-methoxy. In an even more particular embodiment of the first or second aspect, $R^1$ is 2-methyl.

In one embodiment of the first or second aspect, $R^1$ is $NR^{1a}R^{1b}$ and $R^{1a}$ and $R^{1b}$ are independently selected from hydrogen and $C_{1-4}$ alkyl, or $R^{1a}$ and $R^{1b}$ together with the nitrogen atom to which they are attached form a 4 to 6 membered heterocyclic ring. In another embodiment of the first or second aspect, $R^{1a}$ and $R^{1b}$ are $C_{1-4}$ alkyl, or $R^{1a}$ and $R^{1b}$ together with the nitrogen atom to which they are attached form a 4 or 5 membered heterocyclic ring. In one particular embodiment of the first or second aspect, $R^{1a}$ and $R^{1b}$ are $C_{1-4}$ alkyl, or $R^{1a}$ and $R^{1b}$ together with the nitrogen atom to which they are attached form a morpholinyl, pyrrolidinyl or azetidinyl ring. In a more particular embodiment of the first or second aspect, $R^{1a}$ and $R^{1b}$ are $C_{1-4}$ alkyl. In an even more particular embodiment of the first or second aspect, $R^{1a}$ and $R^{1b}$ are selected from methyl and ethyl. In an even more particular embodiment, $R^{1a}$ and $R^{1b}$ together with the nitrogen atom to which they are attached form a morpholinyl, pyrrolidinyl or azetidinyl ring.

In one embodiment of the first or second aspect, n is 0 or 1. In another embodiment of the first or second aspect, n is 1. In a further embodiment of the first or second aspect, n is 0.

In one embodiment of the first or second aspect, $R^2$ is methyl. In another embodiment of the first or second aspect, $R^2$ is methyl and m is 1. In a particular embodiment of the first or second aspect, the compound of formula (I) is a compound of formula (Ia)

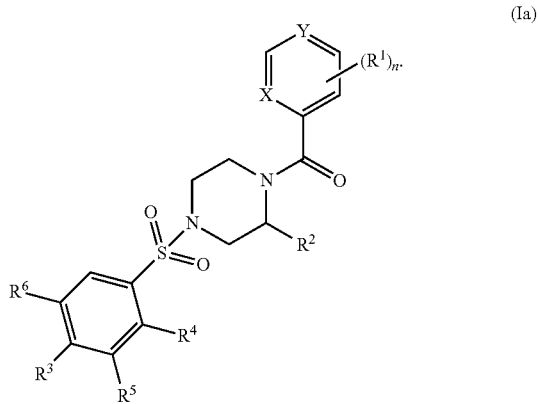

(Ia)

In a more particular embodiment of the first or second aspect, the compound of formula (I) is a compound of formula (Ib)

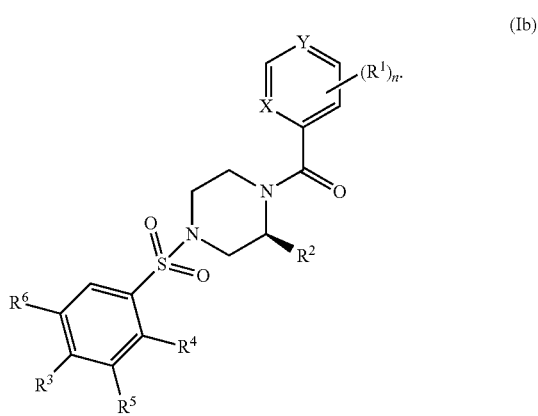

(Ib)

In one embodiment of the first or second aspect, $R^3$ is $C_{1-4}$ haloalkyl or $C_{1-4}$ haloalkoxy. In one particular embodiment of the first or second aspect, $R^3$ is trifluoromethyl, trifluoromethoxy or difluoromethoxy. In a more particular embodiment of the first or second aspect, $R^3$ is trifluoromethyl.

In one embodiment of the first or second aspect, $R^4$ is hydrogen or methyl. In one particular embodiment of the first or second aspect, $R^4$ is hydrogen.

In one embodiment of the first or second aspect, $R^5$ and $R^6$ are independently selected from hydrogen and $C_{1-4}$ haloalkyl. In one particular embodiment of the first or second aspect, $R^5$ and $R^6$ are independently selected from hydrogen and trifluoromethyl. In a more particular embodiment of the first or second aspect, $R^5$ and $R^6$ are hydrogen.

In one embodiment of the first or second aspect, X is nitrogen and Y is carbon, or X is carbon and Y is nitrogen; $R^1$ is $C_{1-4}$ alkyl, $C_{1-4}$ alkoxy, cyano or $NR^{1a}R^{1b}$, particularly $R^1$ is $C_{1-4}$ alkyl or $C_{1-4}$ alkoxy, more particularly $R^1$ is methyl or methoxy, even more particularly $R^1$ is selected from 2-methyl, 6-methyl, 2-methoxy and 6-methoxy, yet even more particularly $R^1$ is 2-methyl; n is 0 or 1, particularly n is 1; $R^2$ is methyl, particularly $R^2$ is methyl and m is 1, more particularly 2-methyl relative to the piperazine carbonyl bond (as in formula (Ia)), even more particularly (2S)-2-methyl (as in formula (Ib)); $R^3$ is $C_{1-4}$ haloalkyl or $C_{1-4}$ haloalkoxy, particularly $R^3$ is trifluoromethyl, trifluoromethoxy or difluoromethoxy, more particularly $R^3$ is trifluoromethyl; $R^4$ is hydrogen or methyl, particularly $R^4$ is hydrogen; $R^5$ and $R^6$ are independently selected from hydrogen and $C_{1-4}$ haloalkyl, particularly $R^5$ and $R^6$ are independently selected from hydrogen and trifluoromethyl, more particularly $R^5$ and $R^6$ are hydrogen.

In one embodiment of the first or second aspect, X is nitrogen and Y is carbon, or X is carbon and Y is nitrogen; $R^1$ is $C_{1-4}$ alkyl, $C_{1-4}$ alkoxy, cyano or $NR^{1a}R^{1b}$; n is 0 or 1; when present, $R^2$ is methyl; $R^3$ is $CO_{1-4}$ haloalkyl or $C_{1-4}$ haloalkoxy; $R^4$ is hydrogen or methyl; $R^5$ and $R^6$ are independently selected from hydrogen and $C_{1-4}$ haloalkyl.

In one embodiment of the first or second aspect, X is nitrogen and Y is carbon, or X is carbon and Y is nitrogen; $R^1$ is $C_{1-4}$ alkyl or $C_{1-4}$ alkoxy; n is 1; $R^2$ is methyl and m is 1; $R^3$ is trifluoromethyl, trifluoromethoxy or difluoromethoxy; $R^4$ is hydrogen; $R^5$ and $R^6$ are independently selected from hydrogen and trifluoromethyl.

In one embodiment of the first or second aspect, X is nitrogen and Y is carbon, or X is carbon and Y is nitrogen; $R^1$ is methyl or methoxy; n is 1; $R^2$ is 2-methyl relative to the piperazine carbonyl bond (as in formula (Ia)) and m is 1; $R^3$ is trifluoromethyl, trifluoromethoxy or difluoromethoxy; $R^4$ is hydrogen; $R^5$ and $R^6$ are hydrogen.

In one embodiment of the first or second aspect, X is nitrogen and Y is carbon, or X is carbon and Y is nitrogen; $R^1$ is selected from 2-methyl, 6-methyl, 2-methoxy and 6-methoxy; n is 1; $R^2$ is (2S)-2-methyl (as in formula (Ib)) and m is 1; $R^3$ is trifluoromethyl, trifluoromethoxy or difluoromethoxy; $R^4$ is hydrogen; $R^5$ and $R^6$ are hydrogen.

In one embodiment of the first or second aspect, X is nitrogen and Y is carbon, or X is carbon and Y is nitrogen; $R^1$ is $NR^{1a}R^{1b}$ and $R^{1a}$ and $R^{1b}$ are independently hydrogen or $C_{1-4}$ alkyl, or $R^{1a}$ and $R^{1b}$ together with the nitrogen atom to which they are attached form a 4 to 6 membered heterocyclic ring, particularly $R^{1a}$ and $R^{1b}$ are independently $C_{1-4}$ alkyl, or $R^{1a}$ and $R^{1b}$ together with the nitrogen atom to which they are attached form a 4 or 5 membered heterocyclic ring, more particularly $R^{1a}$ and $R^{1b}$ are $C_{1-4}$ alkyl, or $R^{1a}$ and $R^{1b}$ together with the nitrogen atom to which they are attached form a morpholinyl, pyrrolidine or azetidinyl ring, even more particularly $R^{1a}$ and $R^{1b}$ are $C_{1-4}$ alkyl, yet even more particularly $R^{1a}$ and $R^{1b}$ are selected from methyl and ethyl; n is 0 or 1, particularly n is 1; $R^2$ is methyl, particularly $R^2$ is methyl and m is 1, more particularly 2-methyl relative to the piperazine carbonyl bond (as in formula (Ia)), even more particularly (2S)-2-methyl (as in formula (Ib)); $R^3$ is $C_{1-4}$ haloalkyl or $C_{1-4}$ haloalkoxy, particularly $R^3$ is trifluoromethyl, trifluoromethoxy or difluoromethoxy, more particularly $R^3$ is trifluoromethyl; $R^4$ is hydrogen or methyl, particularly $R^4$ is hydrogen; $R^5$ and $R^6$ are independently selected from hydrogen and $C_{1-4}$ haloalkyl, particularly $R^5$ and $R^6$ are independently selected from hydrogen and trifluoromethyl, more particularly $R^5$ and $R^6$ are hydrogen.

In one embodiment of the first or second aspect, X is nitrogen and Y is carbon, or X is carbon and Y is nitrogen; $R^1$ is $NR^{1a}R^{1b}$ and $R^{1a}$ and $R^{1b}$ are independently hydrogen or $C_{1-4}$ alkyl, or $R^{1a}$ and $R^{1b}$ together with the nitrogen atom to which they are attached form a 4 to 6 membered heterocyclic ring; n is 0 or 1; when present, $R^2$ is methyl; $R^3$ is $C_{1-4}$ haloalkyl or $C_{1-4}$ haloalkoxy; $R^4$ is hydrogen or methyl; $R^5$ and $R^6$ are independently selected from hydrogen and $C_{1-4}$ haloalkyl.

In one embodiment of the first or second aspect, X is nitrogen and Y is carbon, or X is carbon and Y is nitrogen; $R^{1a}$ and $R^{1b}$ are independently $C_{1-4}$ alkyl, or $R^{1a}$ and $R^{1b}$ together with the nitrogen atom to which they are attached form a 4 or 5 membered heterocyclic ring; n is 1; $R^2$ is methyl and m is 1; $R^3$ is trifluoromethyl, trifluoromethoxy or difluoromethoxy; $R^4$ is hydrogen or methyl; $R^5$ and $R^6$ are independently selected from hydrogen and trifluoromethyl.

In one embodiment of the first or second aspect, X is nitrogen and Y is carbon, or X is carbon and Y is nitrogen; $R^{1a}$ and $R^{1b}$ are $C_{1-4}$ alkyl, or $R^{1a}$ and $R^{1b}$ together with the nitrogen atom to which they are attached form a morpholinyl, pyrrolidine or azetidinyl ring, n is 1; $R^2$ is 2-methyl relative to the piperazine carbonyl bond; $R^3$ is trifluoromethyl, trifluoromethoxy or difluoromethoxy; $R^4$ is hydrogen; $R^5$ and $R^6$ are independently selected from hydrogen.

In one embodiment of the first or second aspect, the compound is selected from a compound of Examples 1 to 16, or a salt thereof.

In a third aspect, the compound is a compound of formula (Ic), or a pharmaceutically acceptable salt thereof, for use in therapy, wherein

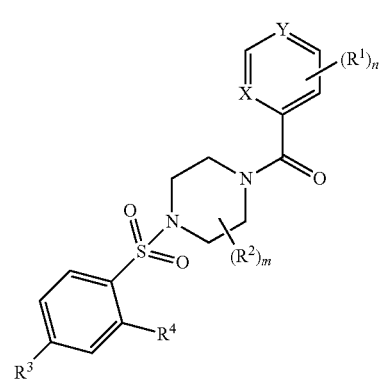

(Ic)

X is nitrogen and Y is carbon, or X is carbon and Y is nitrogen; $R^1$ represents $C_{1-4}$ alkyl, $C_{1-4}$ alkoxy, cyano or morpholinyl; m and n independently represent an integer from 0 to 1; $R^2$ represents $C_{1-4}$ alkyl;

R³ represents halogen, cyano, trifluoromethyl, trifluoromethoxy or difluoromethoxy;
R⁴ represents hydrogen or methyl;
such that when R³ represents cyano, R⁴ represents a group other than hydrogen.

In a fourth aspect, the compound is a compound of formula (Ic), or a salt thereof, wherein
X is nitrogen and Y is carbon, or X is carbon and Y is nitrogen;
R¹ represents $C_{1-4}$ alkyl, $C_{1-4}$ alkoxy, cyano or morpholinyl;
m and n independently represent an integer from 0 to 1;
R² represents $C_{1-4}$ alkyl;
R³ represents halogen, cyano, trifluoromethyl, trifluoromethoxy or difluoromethoxy;
R⁴ represents hydrogen or methyl;
such that when R³ represents cyano, R⁴ represents a group other than hydrogen;
with the proviso that the compound is not
1-[(4-chlorophenyl)sulfonyl]-4-(2-pyridinylcarbonyl)piperazine;
1-[(4-chlorophenyl)sulfonyl]-4-(4-pyridinylcarbonyl)piperazine;
1-(4-pyridinylcarbonyl)-4-{[4-(trifluoromethyl)phenyl]sulfonyl}piperazine;
1-(2-pyridinylcarbonyl)-4-{[4-(trifluoromethyl)phenyl]sulfonyl}piperazine;
1-(2-pyridinylcarbonyl)-4-({4-[(trifluoromethyl)oxy]phenyl}sulfonyl)piperazine; and
1-(4-pyridinylcarbonyl)-4-({4-[(trifluoromethyl)oxy]phenyl}sulfonyl)piperazine.

In one embodiment of the third or fourth aspect, X is nitrogen and Y is carbon, or X is carbon and Y is nitrogen. In another embodiment of the third or fourth aspect, X is nitrogen and Y is carbon. In a further embodiment of the third or fourth aspect, X is carbon and Y is nitrogen.

In one embodiment of the third or fourth aspect, n represents 0 or 1. In a further embodiment of the third or fourth aspect, n represents 1. When present, in one embodiment of the third or fourth aspect, R¹ represents $C_{1-4}$ alkyl, $C_{1-4}$ alkoxy or cyano. In a further embodiment of the third or fourth aspect, R¹ represents $C_{1-4}$ alkyl. In a yet further embodiment of the third or fourth aspect, R¹ represents methyl, particularly 2-methyl or 6-methyl, even more particularly 2-methyl.

In one embodiment of the third or fourth aspect, m represents 0 or 1. In a further embodiment of the third or fourth aspect, m represents 1.

When present, in one embodiment of the third or fourth aspect, R² represents $C_{1-3}$ alkyl. In a further embodiment of the third or fourth aspect, R² represents methyl or ethyl. In a yet further embodiment of the third or fourth aspect, R² represents methyl.

In one embodiment of the third or fourth aspect, R³ represents chlorine, cyano, trifluoromethyl, trifluoromethoxy or difluoromethoxy. In a further embodiment of the third or fourth aspect, R³ represents trifluoromethyl.

Certain compounds as defined in the first to fourth aspect may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, J. Pharm. Sci., 1977, 66, 1-19. The term "pharmaceutically acceptable salts" includes salts prepared from pharmaceutically acceptable acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

Examples of pharmaceutically acceptable salts include those formed from maleic, fumaric, benzoic, ascorbic, pamoic, succinic, hydrochloric, sulfuric, bismethylenesalicylic, methanesulfonic, ethanedisulfonic, propionic, tartaric, salicylic, citric, gluconic, aspartic, stearic, palmitic, itaconic, glycolic, p-aminobenzoic, glutamic, benzenesulfonic, cyclohexylsulfamic, phosphoric and nitric acids.

It will be appreciated by those skilled in the art that certain protected derivatives of the compounds as defined in the first to fourth aspect, which may be made prior to a final deprotection stage, may not possess pharmacological activity as such, but may, in certain instances, be administered orally or parenterally and thereafter metabolised in the body to form compounds as defined in the first to fourth aspect which are pharmacologically active. Such derivatives may therefore be described as "prodrugs". All protected derivatives and prodrugs of compounds defined in the first to fourth aspect are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within the compounds as defined in the first and second aspects. Therefore, in a further aspect, the invention provides a prodrug of a compound as defined in the first to fourth aspect.

It will be appreciated that certain compounds as defined in the first to fourth aspect, or their salts, may exist as solvates, such as hydrates. Where solvates exist, this invention includes within its scope stoichiometric and non-stoichiometric solvates.

It will be appreciated that certain compounds as defined in the first to fourth aspect, or their salts, may exist in more than one polymorphic form. The invention extends to all such forms whether in a pure polymorphic form or when admixed with any other material, such as another polymorphic form.

Certain compounds as defined in the first to fourth aspect are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The subject invention also includes isotopically-labelled compounds, which are identical to the compounds as defined in the first to fourth aspect, but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, fluorine, such as $^3H$, $^{11}C$, $^{14}C$ and $^{18}F$.

Compounds as defined in the first to fourth aspect and salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography). PET is useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labelled reagent. In one embodiment, compounds as defined in the first to fourth aspect or salts thereof are not isotopically labelled.

Throughout the specification, general formulae are designated by Roman numerals (I), (II), (III), (IV), etc. Subsets of these general formulae are defined as (Ia), (Ib), (Ic), etc. . . . (IVa), (IVb), (IVc), etc.

Compounds as defined in the first to fourth aspect may be prepared as set forth in the following Schemes and in the examples. The following processes form another aspect of the present invention.

The present invention also provides a process for the preparation of a compound as defined in the first to fourth aspect, or a salt thereof, which process comprises:

(a) reacting a compound of formula (II)

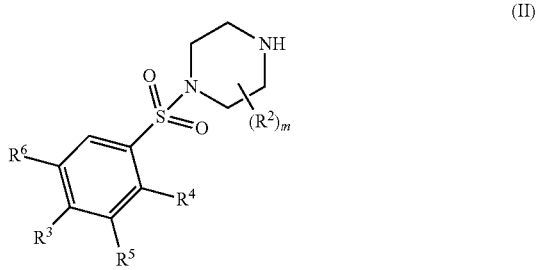

(II)

or a derivative thereof, with a compound of formula (III)

(III)

wherein $R^1$, $R^2$, $R^3$, $R^4$, $R^5$, $R^6$, X, Y, m and n are as defined above and $L^1$ represents a suitable leaving group such as a halogen atom (e.g. chlorine or bromine) or a hydroxyl group activated by commercially available amide coupling reagents (for example, HOBT, HBTU or HATU);

(b) reacting a compound of formula (IV)

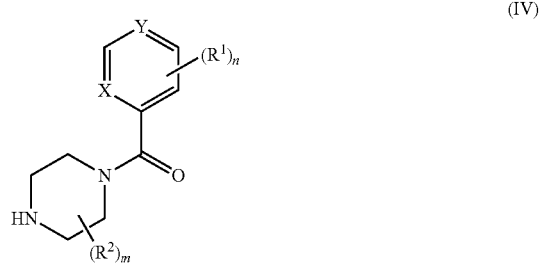

(IV)

with a compound of formula (V)

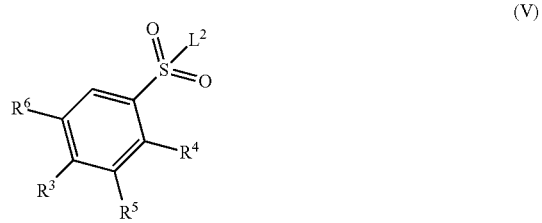

(V)

wherein $R^1$, $R^2$, $R^3$, $R^4$, $R^5$, $R^6$, X, Y, m and n are as defined above and $L^2$ represents a suitable leaving group such as a halogen atom (e.g. chlorine or bromine);

(c) interconversion to other compounds as defined in the first to fourth aspect.

Process (a) typically comprises reaction of a compound of formula (II) with a compound of formula (III) in a suitable solvent such as acetonitrile, tetrahydrofuran, N,N-dimethylformamide or dichloromethane, in the presence of a suitable base, (for example, triethylamine, di-isopropylethylamine or DIPEA) at 0° C. to ambient temperature (for example, room temperature).

Process (b) typically comprises reaction of a compound of formula (IV) and (V) in the presence of a suitable solvent (such as dichloromethane or acetonitrile) in the presence of a suitable base, (for example triethylamine, di-isopropylethylamine or DIPEA) at 0° C. to ambient temperature (for example, room temperature). Alternatively, process (b) may typically comprise reaction of the intermediates in the presence of a suitable base as a solvent (for example pyridine).

Process (c) may be performed using conventional interconversion procedures such as epimerisation, oxidation, reduction, alkylation, nucleophilic or electrophilic aromatic substitution. One such example of interconversion may be interconversion of a compound as defined in the first to fourth aspect wherein $R^3$ represents bromine to a compound as defined in the first to fourth aspect wherein $R^3$ represents cyano. Such interconversion may be carried out by treating the bromine compound with a cyanide salt (for example copper (I) cyanide) in a suitable solvent (such as N,N-dimethylformamide) at elevated temperatures (such as 200° C. using microwave irradiation). Alternatively the interconversion may be carried out using a cyanide salt (for example zinc cyanide) in the presence of a source of a palladium catalyst (for example tris(dibenzylideneacetone)dipalladium(0) and ligand (for example 1, 1'-bis(diphenylphosphino)ferrocene) in a suitable solvent (such as N,N-dimethylformamide) at elevated temperatures (such as 120° C.). This kind of interconversion may also be carried out on intermediates of compounds as defined in the first to fourth aspect, for example on compounds of formula (VII). Another example of interconversion is from a compound of formula (VII) where $R^4$ represents bromine to a compound where $R^4$ represents methyl. Such interconversion may be carried out by treating the bromine compound with a methylboronic acid or ester (eg trimethylboroxin) in the presence of a palladium catalyst (for example tetrakistriphenylphosphine palladium (0)) in a suitable solvent (such as 1,4-dioxane) at elevated temperatures (such as 100° C.).

A different example of an interconversion to other compounds as defined in the first to fourth aspect is shown in the Scheme below:

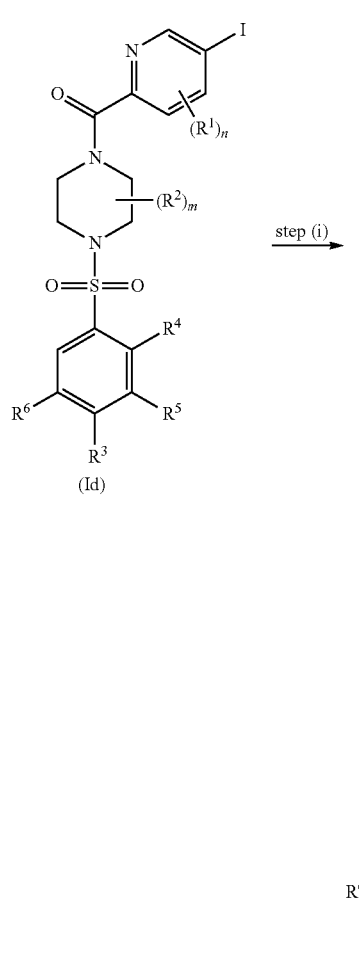

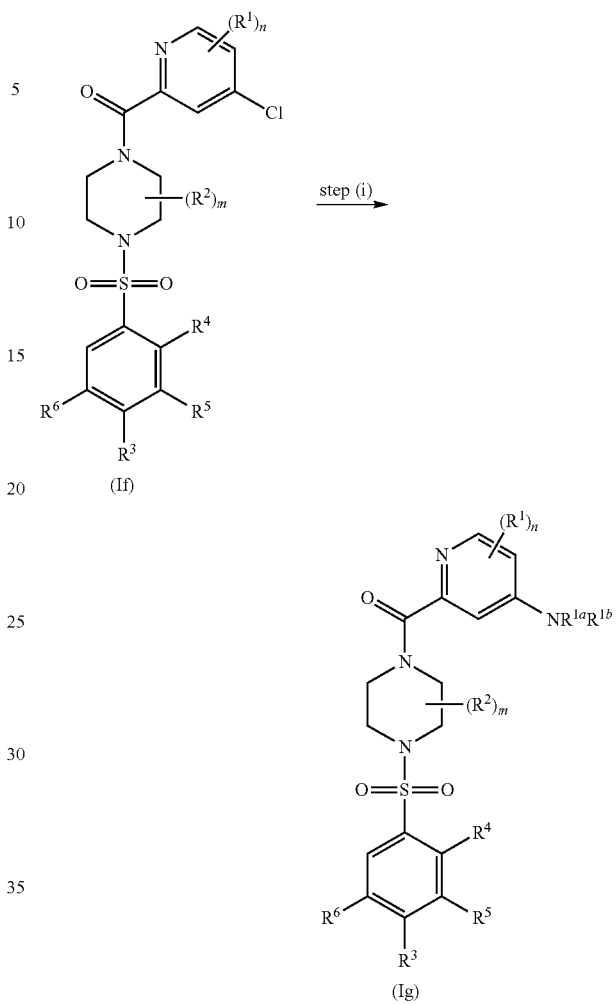

wherein $R^1$, $R^{1a}$, $R^{1b}$, $R^2$, $R^3$, $R^4$, $R^5$, $R^6$ and m are as defined above, and n is 0 or 1.

Step (i) typically comprises reacting a compound of formula (If) with an amine $HNR^{1a}R^{1b}$ in a suitable solvent such as isopropanol in the microwave in the temperature range 100-180° C. for the time required to achieve good conversion to (Ig), such as, for example, 1 h to 48 h.

Compounds of formula (II) may be prepared in accordance with the following Scheme:

wherein $R^1$, $R^2$, $R^3$, $R^4$, $R^5$, $R^6$ and m are as defined above, n is 0 or 1, and Q is $C_{1-4}$ alkyl or $C_{3-6}$ cycloalkyl.

Step (i) typically comprises reacting a compound of formula (Id) with a $C_{1-4}$ alkylzinc halide in the presence of a catalyst such as $PdCl_2(dppf)$ in a suitable solvent such as 1,4-dioxane at an elevated temperature (such as 100° C.). Alternatively, step (i) may comprise reacting a compound of formula (Id) with a suitable $C_{1-4}$ alkylboronic acid or $C_{3-6}$ cycloalkylboronic acid in the presence of a catalyst such as palladium(II) acetate, ligand such as tricyclohexylphosphine and base such as potassium phosphate in a solvent such as a mixture of toluene and water at an elevated temperature.

A further example of an interconversion to other compounds as defined in the first to fourth aspect is shown in the Scheme below:

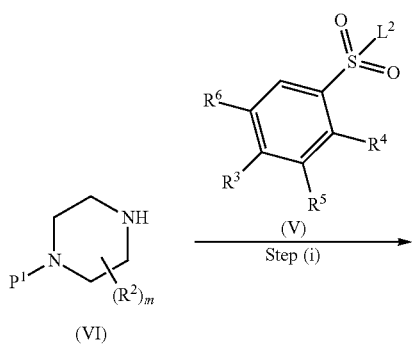

-continued

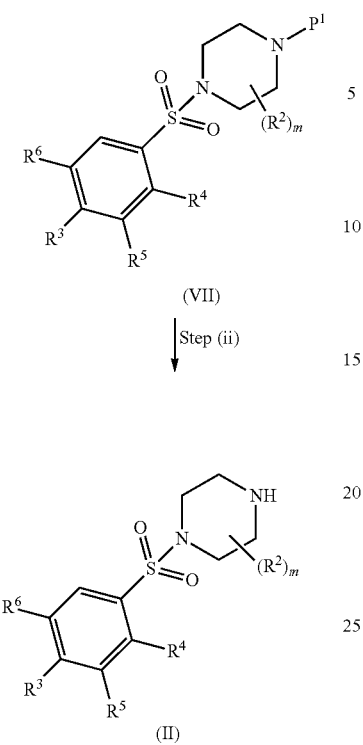

(VII)

Step (ii)

(II)

wherein $R^2$, $R^3$, $R^4$, $R^5$, $R^6$, m and $L^2$ are as defined above and $P^1$ represents a suitable protecting group such as t-butoxycarbonyl. Alternatively, if $P^1$ is H then step (ii) is not required.

Step (i) typically comprises reacting a compound of formula (V) and (VI) in a suitable solvent, such as DCM or MeCN in the presence of a base, (for example triethylamine, di-isopropylethylamine or DIPEA) at 0° C. to ambient temperature (for example ambient temperature). Alternatively, step (i) may typically be carried out using a suitable base as a solvent, for example pyridine, or step (i) may also be carried out in a solvent mixture of THF and water, using a suitable base such as sodium hydroxide.

Step (ii) typically comprises a deprotection reaction. For example, when $P^1$ represents t-butoxycarbonyl, step (ii) will typically comprise treatment with an acid, for example hydrochloric acid or trifluoroacetic acid, in a solvent (such as 1,4-dioxane, dichloromethane or a mixture of methanol and 1,4-dioxane).

Compounds of formula (IV) may be prepared in accordance with the following Scheme:

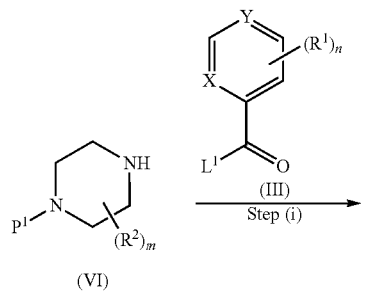

(VI)

-continued

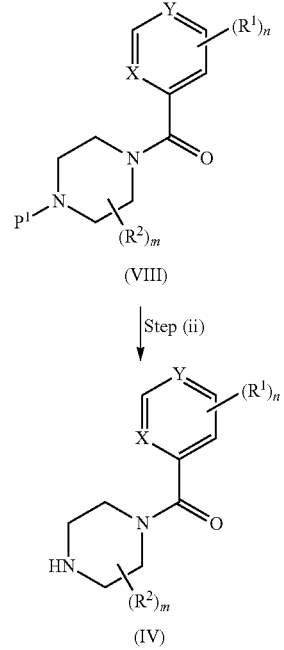

(VIII)

Step (ii)

(IV)

wherein X, Y, $R^2$, m, $R^1$, n and $P^1$ are as defined above.

Step (i) typically comprises reacting a compound of formula (VI) with a compound of formula (III) in a suitable solvent (such as MeCN, THF, DMF or DCM) in the presence of a suitable base (for example, triethylamine, di-isopropylethylamine or DIPEA) at 0° C. to ambient temperature (for example ambient temperature).

Step (ii) typically comprises a deprotection reaction which may be carried out in an analogous manner to Step (ii) above.

Compounds of formula (III), (V) and (VI) are either commercially available, or may be prepared by known methods.

Compounds which can block the $Ca_v2.2$ calcium channels may be useful in the treatment or prophylaxis of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, cancer chemotherapy, headache, toothache and dysmenorrhea.

'Chronic articular pain' conditions include rheumatoid arthritis, osteoarthritis, rheumatoid spondylitis, gouty arthritis and juvenile arthritis.

'Pain associated with functional bowel disorders' includes non-ulcer dyspepsia, non-cardiac chest pain and irritable bowel syndrome.

'Neuropathic pain' syndromes include: diabetic neuropathy, sciatica, non-specific lower back pain, trigeminal neuralgia, multiple sclerosis pain, fibromyalgia, HIV-related neuropathy, post-herpetic neuralgia, trigeminal neuralgia, and pain resulting from physical trauma, amputation, phantom limb syndrome, spinal surgery, cancer, toxins or chronic inflammatory conditions. In addition, neuropathic pain conditions include pain associated with normally non-painful sensations such as "pins and needles" (paraesthesias and dysesthesias), increased sensitivity to touch (hyperesthesia), painful sensation following innocuous stimulation (dynamic, static, thermal or cold allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

Other conditions which could potentially be treated by compounds as defined in the first to fourth aspect include neurodegenerative diseases and neurodegeneration, neurodegeneration following trauma, tinnitus, dependence on a dependence-inducing agent such as opioids (e.g. morphine), CNS depressants (e.g. ethanol), psychostimulants (e.g. cocaine) and nicotine.

Neurodegenerative diseases include dementia, particularly degenerative dementia (including senile dementia, dementia with Lewy bodies, Alzheimer's disease, Pick's disease, Huntingdon's chorea, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment associated with ageing, particularly Age Associated Memory Impairment.

Compounds as defined in the first to fourth aspect may also be useful for neuroprotection and in the treatment or prophylaxis of neurodegeneration following trauma such as stroke, cardiac arrest, pulmonary bypass, traumatic brain injury, spinal cord injury or the like.

Another condition which could potentially be treated by compounds as defined in the first to fourth aspect is spasticity or muscular hypertonicity.

Thus, in an embodiment of the first and third aspect, the therapy is to the treatment or prophylaxis of any of the disorders described herein, in particular pain. In one particular embodiment, the therapy is to the treatment of any of the disorders described herein, in particular pain.

According to a further aspect, there is provided a use of a compound as defined in the first to fourth aspect, or a pharmaceutically acceptable salt thereof, in the manufacture of a medicament for the treatment or prophylaxis of any of the disorders herein, in particular pain. More particularly, there is provided a use of a compound as defined in the first to fourth aspect, or a pharmaceutically acceptable salt thereof, in the manufacture of a medicament for the treatment of any of the disorders herein.

According to another aspect, there is provided a method of treatment or prophylaxis of any of the disorders herein, in particular pain in humans, which method comprises the administration to the human in need of such treatment or prophylaxis, an effective amount of a compound as defined in the first to fourth aspect, or a pharmaceutically acceptable salt thereof.

In the context of the present invention, the term "treatment" refers to symptomatic treatment and the term "prophylaxis" is used to mean preventing symptoms in an already afflicted subject or preventing recurrence of symptoms in an afflicted subject and is not limited to complete prevention of an affliction.

In order to use a compound as defined in the first to fourth aspect or a pharmaceutically acceptable salt thereof for the treatment or prophylaxis of humans and other mammals it is normally formulated in accordance with standard pharmaceutical practice as a pharmaceutical composition. Therefore in another aspect of the invention there is provided a pharmaceutical composition comprising a compound as defined in the first to fourth aspect, or a pharmaceutically acceptable salt thereof, adapted for use in human or veterinary medicine.

In order to use compounds as defined in the first to fourth aspect in therapy, they will normally be formulated into a pharmaceutical composition in accordance with standard pharmaceutical practice. The present invention also provides a pharmaceutical composition, which comprises a compound as defined in the first to fourth aspect, or a pharmaceutically acceptable salt thereof, and optionally a pharmaceutically acceptable excipient.

When used in the treatment or prophylaxis of pain, the compounds as defined in the first to fourth aspect or a pharmaceutically acceptable salt thereof may be used in combination with other medicaments indicated to be useful in the treatment or prophylaxis of pain of neuropathic origin including neuralgias, neuritis and back pain, and inflammatory pain including osteoarthritis, rheumatoid arthritis, acute inflammatory pain, back pain and migraine. Such therapeutic agents include for Compound COX-2 (cyclooxygenase-2) inhibitors, such as celecoxib, deracoxib, rofecoxib, valdecoxib, parecoxib, COX-189 or 2-(4-ethoxy-phenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisphosphonates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists or memantine; ligands for the $\alpha_2\delta$-subunit of voltage gated calcium channels, such as gabapentin, pregabalin and solzira; tricyclic antidepressants such as amitriptyline; neurone stabilising antiepileptic drugs; cholinesterase inhibitors such as galantamine; mono-aminergic uptake inhibitors such as venlafaxine; opioid analgesics; local anaesthetics; $5HT_1$ agonists, such as triptans, for Compound sumatriptan, naratriptan, zolmitriptan, eletriptan, frovatriptan, almotriptan or rizatriptan; nicotinic acetyl choline (nACh) receptor modulators; glutamate receptor modulators, for Compound modulators of the NR2B subtype; $EP_4$ receptor ligands; $EP_2$ receptor ligands; $EP_3$ receptor ligands; $EP_4$ agonists and $EP_2$ agonists; $EP_4$ antagonists; $EP_2$ antagonists and $EP_3$ antagonists; cannabinoid receptor ligands; bradykinin receptor ligands; vanilloid receptor or Transient Receptor Potential (TRP) ligands; and purinergic receptor ligands, including antagonists at $P2X_3$, $P2X_{2/3}$, $P2X_4$, $P2X_7$ or $P2X_{4/7}$; KCNQ/Kv7 channel openers, such as retigabine; Additional COX-2 inhibitors are disclosed in U.S. Pat. Nos. 5,474,995, 5,633,272; 5,466,823, 6,310,099 and 6,291,523; and in WO 96/25405, WO 97/38986, WO 98/03484, WO 97/14691, WO99/12930, WO00/26216, WO00/52008, WO00/38311, WO01/58881 and WO02/18374.

When used in the treatment or prophylaxis of Alzheimer's disease, the compound as defined in the first to fourth aspect or a pharmaceutically acceptable salt thereof may be used in combination with other medicaments indicated to be useful as either disease modifying or symptomatic treatments of Alzheimer's disease.

Suitable examples of such other therapeutic agents may be agents known to modify cholinergic transmission such as $5\text{-HT}_{1A}$ antagonists, (e.g. lecozotan), 5-HT6 antagonists, M1 muscarinic agonists, M2 muscarinic antagonist, acetylcholinesterase inhibitors (e.g tetrahydroaminoacridine, donepezil or rivastigmine), or allosteric modulators, nicotinic receptor agonists or allosteric modulators, symptomatic agents such as 5-HT6 receptor antagonists, e.g. SB742457, H3 receptor antagonists e.g. GSK189254 and GSK239512, 5-HT4 receptor agonist, PPAR agonists, also NMDA receptor antagonists or modulators, also disease modifying agents such as β or γ-secretase inhibitors (e.g. R-flurbiprofen), also AMPA positive modulators and Glycine Transporter Reuptake inhibitors.

When a compound as defined in the first to fourth aspect or a pharmaceutically acceptable salt thereof is used in combination with another therapeutic agent, the compounds may be administered either sequentially or simultaneously by any convenient route.

The invention thus provides, in a further aspect, a combination comprising a compound as defined in the first to fourth aspect or a pharmaceutically acceptable salt thereof together with a further therapeutic agent or agents.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10% to 60% by weight, of the active material, depending on the method of administration. The dose of the compound as defined in the first to fourth aspect or a pharmaceutically acceptable salt thereof used in the treatment or prophylaxis of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks, months, years or even life.

A further aspect to the invention is a pharmaceutical composition comprising 0.05 to 1000 mg of a compound as defined in the first to fourth aspect or a pharmaceutically acceptable salt thereof, 0 to 3 g more suitably 0 to 2 g of at least one pharmaceutically acceptable carrier.

All publications, including but not limited to patents and patent applications, cited in this specification are herein incorporated by reference as if each individual publication were specifically and individually indicated to be incorporated by reference herein as though fully set forth.

Abbreviations

| | |
|---|---|
| Ar: | argon |
| aq.: | aqueous |
| dba: | dibenzylideneacetone |
| DCM: | dichloromethane |
| DIPEA: | N,N-diisopropylethylamine |
| DMF: | N,N-dimethylformamide |
| DMSO: | dimethylsulfoxide |
| DPPF: | 1,1'-bis(diphenylphosphino)ferrocene |
| EDC: | 1-ethyl-3-(3-dimethyllaminopropyl)carbodiimide hydrochloride |
| EtOAc: | ethyl acetate |
| HATU: | O-(7-azabenzotriazol-1-yl)-N,N,N',N'-tetramethyluronium hexafluorophosphate |
| HBTU: | O-benzotriazole-N,N,N',N'-tetramethyl-uronium-hexafluoro-phosphate |
| HOBT: | hydroxybenzotriazole |
| iHex: | isohexane |
| LCMS: | Liquid Chromatography Mass Spectrometry |
| MS: | mass spectrometry |
| MeCN: | acetonitrile |
| MDAP: | mass directed automated preparative liquid chromatography. |
| MeOH: | methanol |
| rt: | room temperature |
| sat.: | saturated |
| SCX: | strong cation exchange chromatography |
| SPE: | solid phase extraction |
| SP4: | Biotage - SP4 ® automated purification system |
| THF: | tetrahydrofuran |
| TFA: | trifluoroacetic acid |
| $Pd_2(dba)_3$: | tris(dibenzylideneacetone)dipalladium(0) |
| $Pd(PPh_3)_4$: | tetrakis(triphenylphosphine)palladium |
| h: | hour(s) |
| min: | minute(s) |
| Boc: | t-butoxycarbonyl |
| $PdCl_2(dppf)_2$: | (1,1'-bis(diphenylphosphino)ferrocene)dichloropalladium(II) |
| API-ES: | atmospheric pressure ionization electro-spray |

EXAMPLES

The preparation of a number of supporting compounds as defined in the first to fourth aspect are described below.

In the procedures that follow, after each starting material, reference to an intermediate is typically provided. This is provided merely for assistance to the skilled chemist. The starting material may not necessarily have been prepared from the batch referred to.

Description 1

1-{[4-(Trifluoromethyl)phenyl]sulfonyl}piperazine

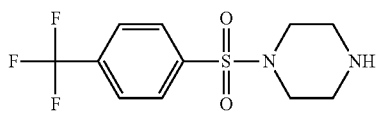 [SMILES: O=S(=O)(c1ccc(C(F)(F)F)cc1)N1CCNCC1]

To a solution of 1,1-dimethylethyl 1-piperazinecarboxylate (5.00 g, 26.8 mmol) in DCM (200 ml) was added DIPEA (9.85 ml, 56.4 mmol) and then 4-(trifluoromethyl)benzenesulfonyl chloride (7.22 g, 29.5 mmol). The reaction mixture was stirred for 1.5 hours at room temperature. The reaction mixture was then reduced to dryness in vacuo, to yield 1,1-dimethylethyl 4-{[4-(trifluoromethyl)phenyl]sulfonyl}-1-piperazinecarboxylate, (crude yield 100%).

m/z (API-ES) 295 [M+H-100]$^+$

To a solution of 1,1-dimethylethyl 4-{[4-(trifluoromethyl)phenyl]sulfonyl}-1-piperazinecarboxylate in 1,4-dioxane (100 ml) was added 4M HCl in 1,4-dioxane (50 ml, 200 mmol) and 3 drops of distilled water. The reaction mixture was stirred overnight. Reaction mixture was then reduced to dryness in vacuo.

The residue was dissolved in DCM (200 ml) and washed with 2M NaOH (50 ml), twice. The organic layer was dried over dried magnesium sulphate, the insolubles removed by filtration, and filtrate reduced to dryness in vacuo to yield the title compound (6.60 g) as a pale yellow solid.

m/z (API-ES) 295 [M+H]$^+$

1H NMR (400 MHz, CHLOROFORM-d) δ ppm 2.89-2.98 (m, 4 H), 2.99-3.09 (m, 4 H), 3.71 (s, 1 H), 7.77-7.85 (m, 2 H), 7.85-7.92 (m, 2 H).

Description 2

(3S)-3-Methyl-1-{[4-(trifluoromethyl)phenyl]sulfonyl}piperazine

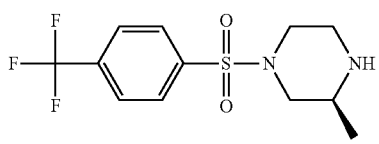 [SMILES: C[C@H]1CN(S(=O)(=O)c2ccc(C(F)(F)F)cc2)CCN1]

To a solution of 1,1-dimethylethyl (2S)-2-methyl-1-piperazinecarboxylate (5.00 g, 25.0 mmol, supplier Small Molecules Inc.) in DCM (200 ml) was added DIPEA (11.4 ml, 65.5 mmol) and 4-(trifluoromethyl)benzenesulfonyl chloride (5.68 g, 23.2 mmol). The reaction mixture was stirred for 1 hour. DCM (200 ml) was added to the reaction mixture which was transferred to a separating funnel. The solution was washed with saturated sodium bicarbonate solution (50 ml, twice) and then with distilled water (50 ml). The organic layer was dried over magnesium sulphate which was removed by filtration and the filtrate was evaporated to dryness on the rotary evaporator to give 8.90 g of white solid. The solid was dissolved in 1,4-dioxane (30 ml) and 4M HCl in 1,4-dioxane (10 ml) and a few drops of water were added and the reaction mixture was stirred for 1 hour. Then further 4M HCl in 1,4-dioxane (20 ml) was added and the reaction stirred overnight. The reaction mixture was evaporated to dryness in vacuo and the residue was dissolved in MeOH and loaded onto an SCX column (Biotage). The column was washed with MeOH (2 column volumes) and the product was eluted with 1M ammonia in MeOH. LCMS showed a large amount of desired product present in the MeOH wash, so this was evaporated to dryness on the rotary evaporator. The residue was dissolved in EtOAc (100 ml) and extracted with 2M aq. HCl (50 ml). The aqueous layer was basified with 2M aqueous NaOH solution until pH remained above 7 and extracted with EtOAc (100 ml). The organic layer was evaporated to dryness on the rotary evaporator to yield the title compound as a white solid (4.34 g).

m/z (API-ES) 309 [M+H]$^+$

1H NMR (400 MHz, MeOH-d$_4$) δ ppm 1.36 (d, J=6.6 Hz, 3 H), 2.62-2.73 (m, 1 H), 2.85-2.97 (m, 1 H), 3.19-3.29 (m, 1 H), 3.45-3.54 (m, 2 H), 3.80-3.95 (m, 2 H), 7.95 (d, J=8.3 Hz, 2 H), 8.05 (d, J=8.3 Hz, 2 H).

Alternative synthesis of (3S)-3-Methyl-1-{[4-(trifluoromethyl)phenyl]sulfonyl}piperazine: Description 2a (2S)-2-methylpiperazine (15 g, 150 mmol) was dissolved in tetrahydrofuran (300 mL) and the solution was cooled down to 0° C. Sodium hydroxide (150 mL, 449 mmol) was added, then 4-(trifluoromethyl)benzenesulfonyl chloride (40 g, 164 mmol) (dissolved in 200 ml THF) was added dropwise and the resulting mixture was stirred for 1 h. Further 4-(trifluoromethyl)benzenesulfonyl chloride (0.06 eq, 2.2 g) was added and mixture stirred for 10 min. The mixture was diluted with DCM (500 ml) and water (500 ml) and stirred for 5 min. The phases were separated, the aqueous layer was extracted with DCM (1000 ml) and the organic phases concentrated under reduced pressure. The residue was taken-up with 1 M HCl (500 ml) and washed with DCM in order to extracted impurities. The aqueous phase was basified to pH=9 with NaOH 3M, extracted with DCM (3×500 ml) and the combined organic phases dried over Na$_2$SO$_4$ before the solvent was removed under reduced pressure to give the title compound (30 g).

m/z (API-ES) 309 [M+H]$^+$

1H NMR (400 MHz, CDCl$_3$) δ ppm 1.06 (d, J=7.2 Hz, 3H), 1.94 (t, J=10.4 Hz, 1H), (td, J=11.2, 4.0 Hz, 1H), 2.88-3.07 (m, 3H), 3.66 (m, 2H), 7.83 (d, J=8.4 Hz, 2H), 7.90 (d, J=8.4 Hz, 2H).

Description 3

1,1-Dimethylethyl (3S)-4-[(4-chlorophenyl)sulfonyl]-3-methyl-1-piperazinecarboxylate

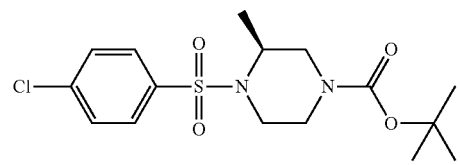 [SMILES: C[C@H]1CN(C(=O)OC(C)(C)C)CCN1S(=O)(=O)c1ccc(Cl)cc1]

To a solution of 1,1-dimethylethyl (3S)-3-methyl-1-piperazinecarboxylate (10.0 g, 49.9 mmol, supplier Aldrich) in pyridine (30 ml) was added 4-chlorobenzenesulfonyl chloride (12.7 g, 59.9 mmol) portionwise. The reaction was stirred at room temperature under an argon atmosphere for 2 hours. The reaction was then evaporated, partitioned between 2N aq. HCl (70 ml) and DCM (80 ml). The aqueous was further extracted with DCM (2×80 ml) and the combined DCM layers were passed through a hydrophobic frit and evaporated. The product was dried under vacuum at 40° C. for 18 hours to yield the title compound as an orange solid (24.14 g).

$^1$H-NMR (400 MHz, CHLOROFORM-d) δ 1.03 (3H, dd, J=6.8, 0.4 Hz), 1.43 (9H, s), 3.05 (1H, m), 3.10 (1H, m), 3.15 (1H, m), 3.60 (1H, m), 3.80 (1H, m), 4.10 (2H, m), 7.48 (2H, m), 7.74 (2H, m).

Description 4

(2S)-1-[(4-Chlorophenyl)sulfonyl]-2-methyl piperazine hydrochloride

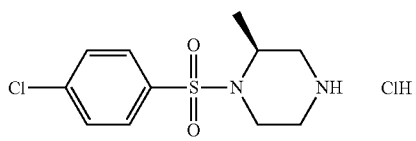 [SMILES: C[C@H]1CNCCN1S(=O)(=O)c1ccc(Cl)cc1 ; Cl]

1,1-Dimethylethyl (3S)-4-[(4-chlorophenyl)sulfonyl]-3-methyl-1-piperazinecarboxylate (may be prepared as described in Description 3) (crude weight 24.14 g, theoretical 49.9 mmol) was suspended in 4M HCl in 1,4-dioxane (80 mL, excess) and stirred vigorously for 3 hours. The sample was evaporated, suspended in diethyl ether (100 mL) and filtered through a sinter. The collected solid was dried under vacuum at 40° C. for 18 hours to yield the title compound as a yellow solid (15.45 g).

m/z (API-ES) 275 [M+H]$^+$ $^1$H NMR (MeOH-d$_4$) δ 1.21 (3H, d, J=7.0 Hz), 2.91-3.45 (5H, br m), 3.89 (1H, m), 4.38 (1H, m), 7.64 (2H, m), 7.88 (2H, m).

Description 5

2,3'-Bipyridine-6'-carboxylic acid

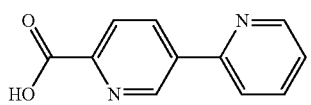

In a 5 ml microwave vial were added 2-bromopyridine (0.093 ml, 0.949 mmol), methyl 5-(4,4,5,5-tetramethyl-1,3,2-dioxaborolan-2-yl)-2-pyridinecarboxylate (300 mg, 1.139 mmol), bis(triphenylphosphine)palladium(II) chloride (133 mg, 0.190 mmol), sodium carbonate (302 mg, 2.85 mmol), 1,2-dimethoxyethane (1.5 ml), ethanol (1.000 ml) and water (0.500 ml). The reaction mixture was heated for 0.5 hours at 120° C. in the microwave. The mixture was diluted with MeOH and filtered through Celite®. The product was concentrated in vacuo then was filtered through a 20 g SCX cartridge (washed with MeOH, eluted with 1M NH$_3$ in MeOH) and evaporated in vacuo. The product was triturated with ether and concentrated under vacuo. The product was diluted in DCM then 1 ml of 1M HCl in ether added and the product was concentrated in vacuo then was dissolved in MeCN/DMSO 1:1 and purified by MDAP. The desired fractions were collected and concentrated under vacuo to give the title compound (44 mg).

m/z (API-ES) 201 [M+H]$^+$

1H NMR (400 MHz, DMSO-d$_6$) δ ppm 7.44-7.52 (m, 1 H) 7.98 (td, J=7.8, 1.8 Hz, 1 H) 8.11-8.19 (m, 2 H) 8.61 (dd, J=8.2, 2.3 Hz, 1 H) 8.73-8.79 (m, 1 H) 9.38 (dd, J=2.2, 0.7 Hz, 1 H) 13.32 (br. s., 1 H).

Description 6

1,1-Dimethylethyl (3R)-3-methyl-4-{[4-(trifluoromethyl)phenyl]sulfonyl}-1-piperazinecarboxylate

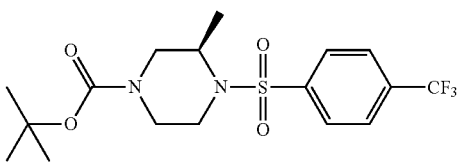 [SMILES: C[C@@H]1CN(C(=O)OC(C)(C)C)CCN1S(=O)(=O)c1ccc(C(F)(F)F)cc1]

To a solution of 1,1-dimethylethyl (3R)-3-methyl-1-piperazinecarboxylate (1.5 g, 7.49 mmol, supplier Aldrich) in DCM (30 ml) was added DIPEA (1.962 ml, 11.23 mmol) and then portionwise addition of 4-(trifluoromethyl)benzenesulfonyl chloride (2.2 g, 8.99 mmol) at room temperature. The resultant mixture was stirred under an atmosphere of Ar for 2 hours before addition of 1M HCl solution (75 ml) and DCM (75 ml). The layers were separated and the aqueous layer was then re-extracted with DCM (75 ml), the organic layers were combined and washed with saturated brine solution (100 ml). The organic layers were then separated, dried (MgSO$_4$) and concentrated to dryness giving the title compound (3.39 g).

m/z (API-ES) 309 [M+H-100]$^+$ $^1$H NMR (400 MHz, CHLOROFORM-d) δ ppm 1.03 (d, J=6.7 Hz, 3 H), 1.43 (s, 9 H), 2.65-3.22 (m, 3 H), 3.54-4.27 (m, 4 H), 7.78 (d, J=8.2 Hz, 2 H), 7.93 (d, J=8.2 Hz, 2 H).

Description 7

(2R)-2-methyl-1-{[4-(trifluoromethyl)phenyl]sulfonyl}piperazine hydrochloride

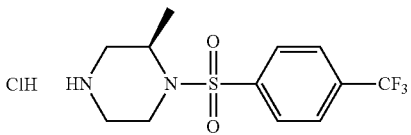 [SMILES: Cl ; C[C@@H]1CNCCN1S(=O)(=O)c1ccc(C(F)(F)F)cc1]

To a solution of 1,1-dimethylethyl (3R)-3-methyl-4-{[4-(trifluoromethyl)phenyl]sulfonyl}-1-piperazinecarboxylate (may be prepared as described in Description 6) (3.39 g, 8.30 mmol) in 1,4-dioxane (20 ml) was added HCl (4M in 1,4-dioxane) (10.37 ml, 41.5 mmol) and the resultant mixture stirred under an atmosphere of Ar for 16 hours. A further 5 ml of 4M HCl in dioxane was added and the mixture stirred at room temperature for 72 hours. The mixture was concentrated to dryness and the residue triturated with diethyl ether and the solid collected by filtration giving the title compound (2.507 g) as a white powder.

m/z (API-ES) 309 [M+H]⁺

1H NMR (400 MHz, DMSO-d$_6$) δ ppm 1.16 (d, J=7.0 Hz, 3H), 2.72-2.86 (m, 1 H), 2.96 (dd, J=13.0, 4.28 Hz, 1 H), 3.08-3.24 (m, 2 H), 3.26-3.34 (m, 1H), 3.70-3.84 (m, 1H), 4.16-4.32 (m, 1H), 8.03 (d, J=8.4 Hz, 2 H), 8.09 (d, J=8.3 Hz, 2 H), 9.16 (br. s. 2H).

Description 8

1,1-Dimethylethyl (3S)-3-methyl-4-{[4-(trifluoromethyl)phenyl]sulfonyl}-1-piperazinecarboxylate

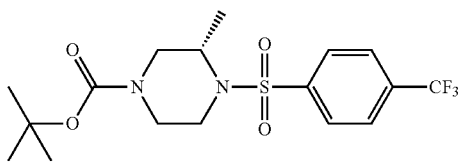 [SMILES: C[C@H]1CN(C(=O)OC(C)(C)C)CCN1S(=O)(=O)c1ccc(C(F)(F)F)cc1]

To a solution of 1,1-dimethylethyl (3S)-3-methyl-1-piperazinecarboxylate (2.05 g, 10.24 mmol) in DCM (50 ml) was added DIPEA (2.68 ml, 15.35 mmol) and the mixture stirred at room temperature for 10 minutes before addition of 4-(trifluoromethyl)benzenesulfonyl chloride (3.00 g, 12.28 mmol) at 0° C. The resultant mixture stirred under an atmosphere of Argon for 16 hours before addition of water (50 ml) and DCM (30 ml). The layers were separated using a hydrophobic frit and the organic layers concentrated to dryness giving the title compound (4.4 g) as a white solid.

m/z (API-ES) 309 [M+H-100]⁺

¹H NMR (400 MHz, CHLOROFORM-d) δ ppm 1.03 (d, J=6.7 Hz, 3 H) 1.43 (s, 9 H) 2.59-3.33 (m, 3 H) 3.43-4.35 (m, 4 H) 7.77 (d, J=8.3 Hz, 2 H) 7.93 (d, J=8.3 Hz, 2 H).

Description 9

(2S)-2-Methyl-1-{[4-(trifluoromethyl)phenyl]sulfonyl}piperazine hydrochloride

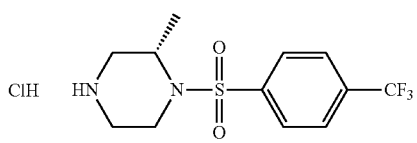 [SMILES: Cl ; C[C@H]1CNCCN1S(=O)(=O)c1ccc(C(F)(F)F)cc1]

To a solution of 1,1-dimethylethyl (3S)-3-methyl-4-{[4-(trifluoromethyl)phenyl]sulfonyl}-1-piperazinecarboxylate (may be prepared as described in Description 7) (4.4 g, 10.77 mmol) in 1,4-dioxane (30 ml) was added HCl (4M in 1,4-dioxane) (5.39 ml, 21.55 mmol) and the mixture stirred at room temperature for 2 hours. A further portion of HCl (4M in 1,4-dioxane) (16.16 ml, 64.6 mmol) was then added and the mixture stirred for a further 16 hours. The volatiles were then removed in vacuo giving the title compound (3.8 g) as a white solid.

m/z (API-ES) 309 [M+H]⁺

¹H NMR (400 MHz, MeOH-d$_4$) δ ppm 1.20 (d, J=7.1 Hz, 3 H) 2.95-3.25 (m, 3 H) 3.36-3.45 (m, 1 H) 3.56-3.77 (m, 1 H) 3.87-4.00 (m, 1 H) 4.34-4.51 (m, 1 H) 7.94 (d, J=8.3 Hz, 2 H) 8.08 (d, J=8.2 Hz, 2 H)

Description 10

1,1-Dimethylethyl (2S)-4-[(4-bromo-2-methylphenyl)sulfonyl]-2-methyl-1-piperazinecarboxylate

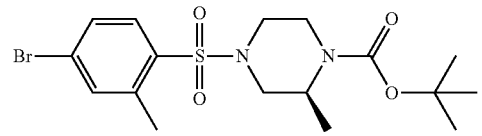

To a solution of 1,1-dimethylethyl (2S)-2-methyl-1-piperazinecarboxylate (2.00 g, 9.99 mmol) and DIPEA (2.62 ml, 14.98 mmol) in dry DCM (25 ml) at 0° C. under Ar was added 4-bromo-2-methylbenzenesulfonyl chloride (2.96 g, 10.98 mmol) and the resulting yellow solution allowed to warm to rt, then stirred at rt for 18 hours. Semi-saturated aq NH$_4$Cl (40 ml) was added, then the aq extracted with DCM (30 ml). The combined organic layers were passed through a hydrophobic frit, then concentrated in vacuo to give a yellow oil (5.01 g). Flash chromatography (silica; Flash 40M; linear gradient (6-50%) EtOAc in isohexane) gave the title compound as a pale yellow oil (3.52 g).

m/z (API-ES) 333 and 335, 1:1, [M+H-100]⁺

¹H NMR (400 MHz, CHLOROFORM-d) δ ppm 1.19 (d, J=6.7 Hz, 3 H), 1.44 (s, 9 H), 2.59 (td, J=12.0, 3.4 Hz, 1 H), 2.61 (s, 3 H), 2.78 (dd, J=12.0, 3.8 Hz, 1 H), 3.11 (td, J=12.0, 3.2 Hz, 1 H), 3.44 (dt, J=12.0, 2.0 Hz, 1 H), 3.59-3.65 (m, 1 H), 3.93 (d, J=12.0 Hz, 1 H), 4.33 (br. s., 1 H), 7.45-7.51 (m, 2 H), 7.72 (d, J=8.4 Hz, 1 H).

Description 11

1,1-Dimethylethyl (2S)-4-[(4-cyano-2-methyl phenyl)sulfonyl]-2-methyl-1-piperazinecarboxylate

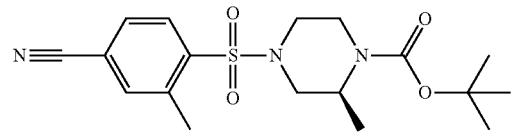 [SMILES: Cc1cc(C#N)ccc1S(=O)(=O)N1CCN(C(=O)OC(C)(C)C)[C@@H](C)C1]

Ar was bubbled through a solution of 1,1-dimethylethyl (2S)-4-[(4-bromo-2-methylphenyl)sulfonyl]-2-methyl-1-piperazinecarboxylate (may be prepared as described in Description 9) (3.51 g, 8.10 mmol) in dry DMF (40 ml) for 0.5 hours, then Zn(CN)$_2$ (0.523 g, 4.45 mmol), Pd$_2$(dba)$_3$ (0.223 g, 0.243 mmol) and DPPF (0.269 g, 0.486 mmol) were added and the resulting brown solution stirred at 120° C. under Ar for 2.5 hours. The mixture was cooled to room temperature, concentrated in vacuo and the residue partitioned between DCM (100 ml) and water (100 ml). The aqueous layer was extracted with DCM (2×100 ml), then the combined organic layers passed through a hydrophobic frit. Concentration gave a brown residue (4.31 g). Flash chromatography (silica; linear gradient (6-50%) EtOAc in isohexane) gave the title compound as a yellow solid (2.88 g).

m/z (API-ES) 280 [M+H-100]⁺

¹H NMR (400 MHz, CHLOROFORM-d) δ ppm 1.20 (d, J=6.8 Hz, 3 H), 1.44 (s, 9 H), 2.65 (td, J=12.0, 3.4 Hz, 1 H), 2.68 (s, 3 H), 2.86 (dd, J=12.0, 4.2 Hz, 1 H), 3.13 (td, J=12.0, 2.8 Hz, 1 H), 3.49 (dt, J=12.0, 1.8 Hz, 1 H), 3.63-3.69 (m, 1 H), 3.95 (d, J=12.0 Hz, 1 H), 4.35 (br. s., 1 H), 7.61-7.65 (m, 2 H), 7.96 (d, J=6.8 Hz, 1 H).

Description 12

3-Methyl-4-{[(3S)-3-methyl-1-piperazinyl]sulfonyl}benzonitrile

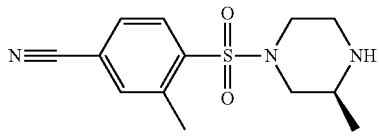 [SMILES: Cc1cc(C#N)ccc1S(=O)(=O)N1CCN[C@@H](C)C1]

A solution of 1,1-dimethylethyl (2S)-4-[(4-cyano-2-methylphenyl)sulfonyl]-2-methyl-1-piperazinecarboxylate (may be prepared as described in Description 10) (2.88 g, 7.59 mmol) and TFA (10 ml, 130 mmol) in dry DCM (10 ml) was stirred at room temperature for 1 hour, then concentrated in vacuo, azeotroping with toluene (25 ml) to give a brown oil. This was partitioned between DCM (50 ml) and saturated aqueous NaHCO₃ (50 ml), then the aqueous layer was extracted with DCM (50 ml). The combined organic layers were passed through a hydrophobic frit and concentrated in vacuo to give the title compound as a yellow oil (2.29 g).

m/z (API-ES) 280 [M+H]⁺

¹H NMR (400 MHz, CHLOROFORM-d) δ ppm 1.06 (d, J=6.4 Hz, 3 H), 2.33 (dd, J=11.6, 10.2 Hz, 1 H), 2.67 (s, 3 H), 2.69-2.75 (td, J=11.5, 3.1 Hz, 1 H), 2.82-2.92 (m, 2 H), 3.03 (dt, J=12.1, 2.6 Hz, 1 H), 3.54-3.65 (m, 2 H), 7.59-7.67 (m, 2 H), 7.99 (d, J=8.6 Hz, 1 H).

Description 13

(3R)-3-Methyl-1-{[4-(trifluoromethyl)phenyl]sulfonyl}piperazine

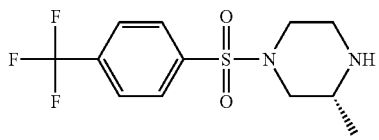 [SMILES: C[C@@H]1CN(S(=O)(=O)c2ccc(C(F)(F)F)cc2)CCN1]

To a solution of 1,1-dimethylethyl (2R)-2-methyl-1-piperazinecarboxylate (2.95 g, 14.73 mmol) in DCM (120 ml) was added DIPEA (5.40 ml, 30.9 mmol) and then 4-(trifluoromethyl)benzenesulfonyl chloride (3.96 g, 16.20 mmol). The reaction mixture was stirred 2.5 hours at room temperature then washed with water (250 ml), dried on a phase separation cartridge and concentrated in vacuo. The obtained product was dissolved in 1,4-dioxane (60 ml) and treated with 4M aq. HCl in 1,4-dioxane (18.41 ml, 73.6 mmol) overnight. The mixture was concentrated under vacuo then dissolved in EtOAc (150 ml), washed with 2N aq. NaOH solution (200 ml) then dried on a phase separation cartridge and concentrated in vacuo. The product was then dissolved in EtOAc (100 ml) and extracted with 2M aq. HCl (2×200 ml). 2M aq. NaOH solution was added to the aqueous layer until basic pH then the product was extracted with EtOAc (500 ml). The organic layer was dried on a phase separation cartridge and concentrated under vacuo to give the title compound (3.76 g).

m/z (API-ES) 309 [M+H]⁺

¹H NMR (400 MHz, CHLOROFORM-d) δ ppm 1.05 (d, J=6.4 Hz, 3 H) 1.93 (t, J=10.6 Hz, 1 H) 2.31 (td, J=11.2, 3.4 Hz, 1 H) 2.86-3.08 (m, 3 H) 3.59-3.73 (m, 2 H) 7.82 (d, J=8.3 Hz, 2 H) 7.89 (d, J=8.2 Hz, 2 H).

Description 14

(3R)-1-[(4-chlorophenyl)sulfonyl]-3-methylpiperazine

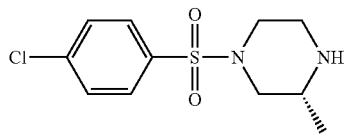 [SMILES: C[C@@H]1CN(S(=O)(=O)c2ccc(Cl)cc2)CCN1]

To a solution of 1,1-dimethylethyl (2R)-2-methyl-1-piperazinecarboxylate (1.5 g, 07.5 mmol) in dry DCM (40 mL) was added triethylamine (2.59 mL, 18.8 mmol) and 4-chlorobenzenesulfonyl chloride (3.15 g, 10.5 mmol) and the reaction stirred at room temperature for 48 h. To the reaction was added resin supported-triamine (5 g) and the mixture stirred for 4 h. The reaction mixture was filtered and the filtrate washed with 0.5 M HCl (aq., 100 mL) followed by water (100 mL) before it was dried (MgSO₄), filtered and the solvent removed in vacuo. The crude product was dissolved in DCM (40 mL) and TFA (10 mL) was added. The solution was stirred for 20 min. The solvent was evaporated and the residue tajen up in DCM (40 mL) and washed with 50% aqueous sodium bicarbonate (100 mL) followed by water (100 mL). The organic phase was dried (MgSO₄), filtered and the solvent removed in vacuo to give the title compound (1.62 g).

m/z (API-ES) 274+276 (3:1) [M+H]⁺

Description 15

(2S)-2-methyl-1-(2-pyridinylcarbonyl)piperazine dihydrochloride

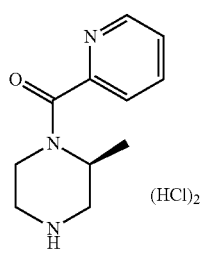

To a solution 1,1-dimethylethyl (3S)-3-methyl-1-piperazinecarboxylate (140 mg, 0.699 mmol) in dichloromethane (5 ml) was added DIPEA (0.183 ml, 1.049 mmol) at room temperature. 2-pyridinecarbonyl chloride (104 mg, 0.735 mmol) was then added and the resultant mixture stirred for 3 h30. The reaction mixture was then diluted with a further 2 ml DCM and 5 ml of water were added and the layers separated, the organics were then washed with 5 ml 2M HCl solution and 5 ml sat NaHCO₃ solution then dried (hydrophobic frit) and concentrated to dryness. To a solution of the resulting 1,1-dimethylethyl (3S)-3-methyl-4-(2-pyridinylcarbonyl)-1-piperazinecarboxylate (78 mg, 0.255 mmol) in 1,4-Dioxane (1 ml) was added HCl (4M in 1,4-Dioxane) (0.319 ml, 1.277 mmol) at room temperature and the resultant mixture stirred overnight at room temperature. Reaction mixture concentrated to dryness and solid triturated with diethylether to give the title compound (71 mg) used without further purification.

m/z (API-ES) 206 [M+H]⁺

Description 16

(2S)-2-methyl-1-[(2-methyl-4-pyridinyl)carbonyl]piperazine

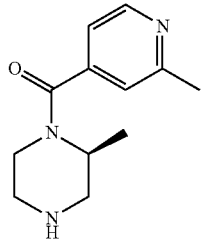 [SMILES: Cc1cc(C(=O)N2CCNC[C@@H]2C)ccn1]

A mixture of 1,1-dimethylethyl (3S)-3-methyl-1-piperazinecarboxylate (146 mg, 0.73 mmol), 2-methyl-4-pyridinecarboxylic acid (100 mg, 0.73 mmol), HBTU (277 mg, 0.73 mmol) HOBT (112 mg, 0.72 mmol) and DIPEA (0.38 mL, 2.19 mmol) in DMF (20 mL) was stirred at room temperature for 12 hours. The reaction mixture was diluted with DCM and extracted with saturated sodium bicarbonate. The organic layer was collected and the solvent was evaporated off using the rotary evaporator. The solvent was difficult to remove so it was azeotroped twice with toluene. The residual solid was dissolved in DCM and purified using SP4. The fractions containing product were combined and evaporated to dryness on the rotary evaporator. The product was dissolved in 1,4-dioxane (7.5 mL) and 4M HCl in dioxane (2.5 mL) was added and the reaction stirred for 3 h. A few drops of water were then added and the mixture stirred for a further 45 min. The solvent was then evaporated off on the rotary evaporator. To remove the water, the residue was azeotroped twice with toluene. The residual solid was dissolved in methanol and transfered to an SCX column. Once loaded, the material was washed with 2 column volumes of methanol. The product was eluted from the column with 2M ammonia in methanol and the solvent removed under vacuum to give the title compound (70 mg).

m/z (API-ES) 220 [M+H]⁺

Description 17

1-[(4-Bromo-2-pyridinyl)carbonyl]-4-{[4-(trifluoromethyl)phenyl]sulfonyl}piperazine

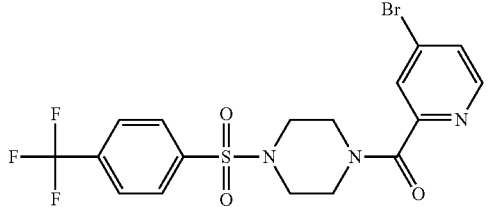 [SMILES: O=C(c1cc(Br)ccn1)N1CCN(S(=O)(=O)c2ccc(C(F)(F)F)cc2)CC1]

To a solution of 1-{[4-(trifluoromethyl)phenyl]sulfonyl}piperazine (200 mg, 0.680 mmol) in DMF (10 ml) was added 4-bromo-2-pyridinecarboxylic acid (137 mg, 0.680 mmol), HOBT.H₂O (104 mg, 0.680 mmol), HBTU (258 mg, 0.680 mmol) and DIPEA (0.356 ml, 2.039 mmol) and the reaction mixture was stirred at room temperature for 2.5 hours. The DMF was evaporated under vacuo then 10 ml of DCM were added and washed with 2M aq. HCl solution (10 ml) saturated aq. NaHCO₃ solution (10 ml) and brine (10 ml), dried on a phase separation cartridge and evaporated in vacuo. The crude material was purified by silica chromatography using a gradient isohexane/EtOAc [100/0] to [50/50] then to [0/100]). The desired fractions were then collected and concentrated to dryness to give 1-[(4-bromo-2-pyridinyl)carbonyl]-4-{[4-(trifluoromethyl)phenyl]sulfonyl}piperazine (171 mg, 0.358 mmol, 52.6% yield).

m/z (API-ES) 478,480 (1:1) [M+H]⁺

1H NMR (400 MHz, CHLOROFORM-d) δ ppm 3.10-3.16 (m, 2 H) 3.17-3.24 (m, 2 H) 3.76-3.85 (m, 2 H) 3.86-3.95 (m, 2 H) 7.54 (dd, J=5.3, 1.9 Hz, 1 H) 7.81-7.87 (m, 3 H) 7.88-7.94 (m, 2 H) 8.35 (d, J=5.3 Hz, 1 H).

Example 1

(2S)-2-Methyl-1-[(3-methyl-2-pyridinyl)carbonyl]-4-{[4-(trifluoromethyl)phenyl]sulfonyl}piperazine hydrochloride

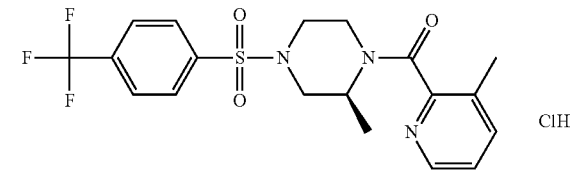 [SMILES: Cc1cccnc1C(=O)N1CCN(S(=O)(=O)c2ccc(C(F)(F)F)cc2)C[C@@H]1C ; Cl]

To a solution of (3S)-3-methyl-1-{[4-(trifluoromethyl)phenyl]sulfonyl}piperazine (Description 2) (100 mg, 0.324 mmol) in DMF (5 ml) was added 3-methyl-2-pyridinecarboxylic acid (44.5 mg, 0.324 mmol), HOBT.H₂O (49.7 mg, 0.324 mmol) and HBTU (123 mg, 0.324 mmol). Finally DIPEA (0.170 ml, 0.973 mmol) was added and the reaction mixture was stirred at room temperature for 20 hours. Solvent was removed by evaporation and MDAP purification yielded the title compound as the formate salt. The formate salt was suspended in sat. sodium bicarbonate and the free amine extracted in to DCM. Evaporation yielded the free base as a clear oil. The oil was treated with 1M ethereal HCl to yield the title compound (115 mg) as a white powder.

m/z (API-ES) 428 [M+H]⁺

1H NMR (400 MHz, CHLOROFORM-d) (NMR of free base; rotameric mixture) δ ppm 1.35 (d, 1.5 H), 1.47 (d, J=7.0 Hz, 1.5 H), 2.27 (s, 1.5 H), 2.30 (s, 1.5 H), 2.35-2.52 (m, 1 H), 2.54-2.67 (m, 1 H), 3.21-3.33 (m, 1 H), 3.37-3.54 (m, 1 H), 3.62-3.72 (m, 1 H), 3.88 (br. s., 1 H), 4.64-4.74 (m, 0.5 H), 5.03-5.15 (m, 0.5 H), 7.22 (dt, J=8.0, 4.5 Hz, 1 H), 7.56 (d, J=7.0 Hz, 1 H), 7.83 (d, J=8.5 Hz, 2 H), 7.87 (d, J=8.5 Hz, 2 H), 8.37 (d, J=4.5 Hz, 1 H).

Example 2

1-[(6-Methyl-2-pyridinyl)carbonyl]-4-{[4-(trifluoromethyl)phenyl]sulfonyl}piperazine

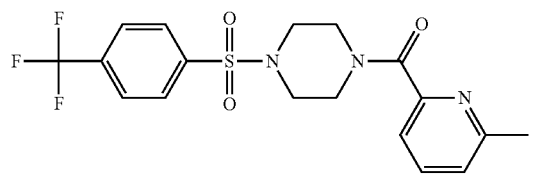 [SMILES: Cc1cccc(C(=O)N2CCN(S(=O)(=O)c3ccc(C(F)(F)F)cc3)CC2)n1]

To a solution of 1-{[4-(trifluoromethyl)phenyl]sulfonyl}piperazine (Description 1) (100 mg, 0.340 mmol) in DMF (5 ml) was added HOBT.H$_2$O (52.0 mg, 0.340 mmol), HBTU (129 mg, 0.340 mmol), 6-methyl-2-pyridinecarboxylic acid (46.6 mg, 0.340 mmol) and DIPEA (0.178 ml, 1.019 mmol). The reaction mixture was stirred for 2 hours at room temperature. Reaction mixture was transferred to a 100 ml round bottom flask and was reduced to dryness in vacuo. The residue was dissolved in DCM (50 ml) and transferred to a separating funnel then was washed with saturated aq. NaHCO$_3$ solution (5 ml), twice. The organic layer was collected and dried with dried magnesium sulphate. The solid was removed by filtration and the filtrate collected in a 250 ml round bottom flask and concentrated to dryness in vacuo. The residue was then dissolved in 1.8 ml 1:1 MeCN/DMSO and purified by MDAP in 2 batches. The fractions containing desired product were combined in a 250 ml round bottom flask and concentrated in vacuo to yield the title compound (99 mg).

m/z (API-ES) 414 [M+H]$^+$

1H NMR (400 MHz, CHLOROFORM-d) δ ppm 2.52 (s, 3 H) 3.03-3.24 (m, 4 H) 3.72-3.79 (m, 2 H) 3.89 (t, J=5.0 Hz, 2 H) 7.19 (d, J=8.0 Hz, 1 H) 7.39 (d, J=7.7 Hz, 1 H) 7.65 (t, J=7.5 Hz, 1 H) 7.78-7.84 (m, 2 H) 7.85-7.95 (m, 2 H).

Example 3

1-[(3-Methyl-2-pyridinyl)carbonyl]-4-{[4-(trifluoromethyl)phenyl]sulfonyl}piperazine

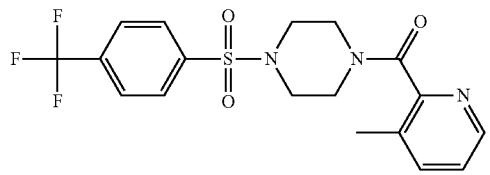 [SMILES: Cc1cccnc1C(=O)N1CCN(S(=O)(=O)c2ccc(C(F)(F)F)cc2)CC1]

To a solution of 1-{[4-(trifluoromethyl)phenyl]sulfonyl}piperazine (Description 1) (100 mg, 0.340 mmol) in DMF (5 ml) was added HOBT.H$_2$O (52.0 mg, 0.340 mmol), HBTU (129 mg, 0.340 mmol), 3-methyl-2-pyridinecarboxylic acid (46.6 mg, 0.340 mmol) and DIPEA (0.178 ml, 1.019 mmol). The reaction mixture was stirred for 2 hours at room temperature. Reaction mixture was transferred to a 100 ml round bottom flask and was reduced to dryness in vacuo. The residue was dissolved in DCM (50 ml) and transferred to a separating funnel then was washed with saturated aq. NaHCO$_3$ solution (5 ml), twice. The organic layer was collected and dried with dried magnesium sulphate. The solid was removed by filtration and the filtrate collected in a 250 ml round bottom flask and reduced to dryness in vacuo. The residue was then dissolved in 1.8 ml 1:1 MeCN/DMSO and purified by MDAP in 2 batches. The fractions containing desired product were combined in a 250 ml round bottom flask and reduced in vacuo to yield the title compound (91 mg).

m/z (API-ES) 414 [M+H]$^+$

1H NMR (400 MHz, CHLOROFORM-d) δ ppm 2.29 (s, 3 H) 3.01-3.10 (m, 2 H) 3.20 (t, J=5.0 Hz, 2 H) 3.30-3.40 (m, 2 H) 3.87-3.98 (m, 2 H) 7.23 (dd, J=8.0, 5.0 Hz, 1 H) 7.52-7.60 (m, 1 H) 7.78-7.92 (m, 4 H) 8.36 (dd, J=5.0, 1.0 Hz, 1 H).

Example 4

(2S)-2-methyl-1-(2-pyridinylcarbonyl)-4-{[4-(trifluoromethyl)phenyl]sulfonyl}piperazine formic acid salt (1:1)

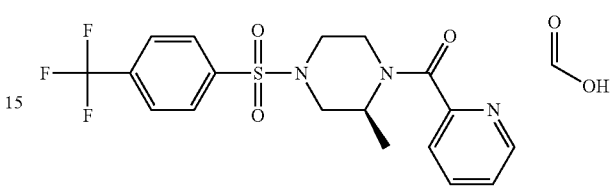

To a solution of (3S)-3-methyl-1-{[4-(trifluoromethyl)phenyl]sulfonyl}piperazine (Description 2) (80 mg, 0.259 mmol) in DMF (5 ml) was added 2-pyridinecarboxylic acid (31.9 mg, 0.259 mmol), HOBT.H$_2$O (39.7 mg, 0.259 mmol), HBTU (98 mg, 0.259 mmol) and DIPEA (0.136 ml, 0.778 mmol) and the reaction mixture was stirred at room temperature overnight. DMF was evaporated in vacuo then 5 ml of DCM were added and washed with saturated NaHCO$_3$ solution (5 ml), dried on a phase separation cartridge and evaporated in vacuo. The crude material was dissolved in MeCN/DMSO 1:1 and purified by MDAP. The desired fractions were collected and concentrated under vacuo giving the title compound (93 mg).

m/z (API-ES) 414 [M+H]$^+$

1H NMR (400 MHz, CHLOROFORM-d) (rotameric mixture) δ ppm 1.45 (br. s., 3 H), 2.47 (t, J=11.0 Hz, 1 H), 2.55-2.70 (m, 1 H), 3.23-3.39 (m, 0.5 H), 3.42-3.62 (m, 1 H), 3.62-3.81 (m, 1 H), 3.82-3.96 (m, 0.5 H), 3.97-4.13 (m, 0.5 H), 4.35-4.51 (m, 0.5 H), 4.54-4.72 (m, 0.5 H), 4.94-5.11 (m, 0.5 H), 7.31-7.42 (m, 1 H), 7.62 (d, J=6.7 Hz, 1 H), 7.76-7.93 (m, 5 H), 8.55 (d, J=4.0 Hz, 1 H).

Example 5

2'-[(4-{[4-(Trifluoromethyl)phenyl]sulfonyl}-1-piperazinyl)carbonyl]-2,4'-bipyridine

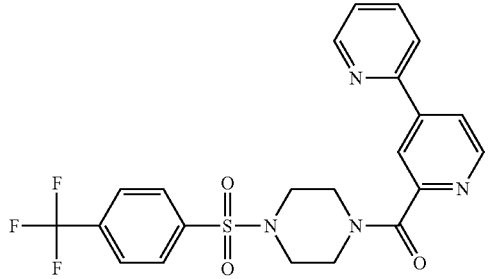 [SMILES: O=C(c1cc(-c2ccccn2)ccn1)N1CCN(S(=O)(=O)c2ccc(C(F)(F)F)cc2)CC1]

In a 5 ml microwave vial were added 1-[(4-bromo-2-pyridinyl)carbonyl]-4-{[4-(trifluoromethyl)phenyl]sulfonyl}piperazine (Description 17) (150 mg, 0.314 mmol), 2-(4,4,5,5-tetramethyl-1,3,2-dioxaborolan-2-yl)pyridine (Description 5) (129 mg, 0.627 mmol), bis(triphenylphosphine)palladium(II) chloride (44.0 mg, 0.063 mmol), sodium carbonate (100 mg, 0.941 mmol), 1,2-dimethoxyethane (1.5 ml), ethanol (1.0 ml) and water (0.50 ml). The reaction mixture was heated for 20 minutes at 120° C. in the microwave. The crude material was diluted in EtOH and filtered through celite. The filtrate was concentrated in vacuo then diluted with MeOH and filtered through an SCX cartridge (1 g). All material came out with MeOH wash so product concentrated, diluted with MeOH and filtered through a 5 g SCX column (washed with MeOH, eluted with $NH_3$ 0.5M in MeOH). The eluted product was concentrated in vacuo then dissolved in MeCN/DMSO 1:1 and purified by MDAP. The desired fractions were combined and concentrated under vacuo to give the title compound (2 mg).

m/z (API-ES) 477 [M+H]$^+$

1H NMR (400 MHz, CHLOROFORM-d) δ ppm 3.08-3.18 (m, 2 H), 3.18-3.26 (m, 2 H), 3.79-3.87 (m, 2 H), 3.90-4.00 (m, 2 H), 7.35-7.40 (m, 1 H), 7.81-7.87 (m, 4 H), 7.88-7.94 (m, 2 H), 8.01 (dd, J=5.2, 1.8 Hz, 1 H), 8.22-8.24 (m, 1 H), 8.65 (dd, J=5.2, 0.8 Hz, 1 H), 8.72-8.76 (m, 1 H).

Example 6

(2S)-1-[(4-Chlorophenyl)sulfonyl]-2-methyl-4-(2-pyridinylcarbonyl)piperazine hydrochloride

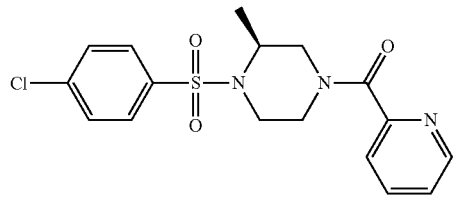

To a solution of (2S)-1-[(4-chlorophenyl)sulfonyl]-2-methylpiperazine hydrochloride (Description 4) (200 mg, 0.728 mmol) in DCM (8 mL) was added triethylamine (0.172 ml, 1.237 mmol) and the reaction was cooled to 0° C. and stirred under argon. 2-pyridinecarbonyl chloride (155 mg, 0.873 mmol) was added portionwise and the reaction was slowly allowed to warm to rt, stirring continued for 18 hours. The sample was evaporated, the crude residue was purified by silica chromatography (5 g silica SPE), (eluting a gradient from 20-90% ethyl acetate in hexane) and the product containing fractions were concentrated. The product was then dissolved in 1,4-dioxane (2 ml) to this was added 1M ethereal HCl (4 ml) the sample was evaporated and then triturated in diethyl ether until solid. The solid was dried under vacuum at 40° C. for 18 hours to yield the title compound as a white solid (110 mg)

m/z (API-ES) 380 [M+H]$^+$ $^1$H NMR (MeOH-$d_4$) δ 1.07 (3H, br m), 3.04-4.35 (7H, br. m), 7.62 (2H, m), 7.87 (2H, m), 7.90-8.00 (2H, br m), 8.38 (1H, m), 8.80 (1H, m).

Example 7

6'[(4-{[4-(Trifluoromethyl)phenyl]sulfonyl}-1-piperazinyl)carbonyl]-2,3'-bipyridine

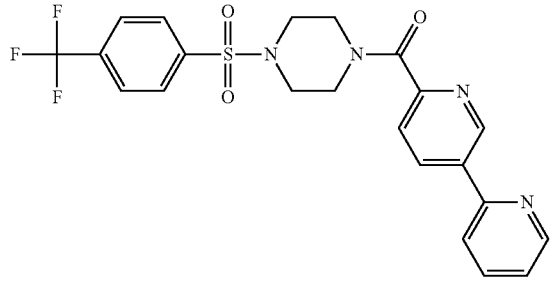 [SMILES: O=C(c1ccc(-c2ccccn2)cn1)N1CCN(S(=O)(=O)c2ccc(C(F)(F)F)cc2)CC1]

To a solution of 1-{[4-(trifluoromethyl)phenyl]sulfonyl}piperazine (Description 1) (64.7 mg, 0.220 mmol) in DMF (3 ml) was added 2,3'-bipyridine-6'-carboxylic acid (Description 5) (44 mg, 0.220 mmol), HOBT.H$_2$O (33.7 mg, 0.220 mmol), HBTU (83 mg, 0.220 mmol) and DIPEA (0.115 ml, 0.659 mmol) and the reaction mixture was stirred at room temperature for 1 h. The reaction mixture was concentrated under vacuum then DCM was added (5 ml) and washed with saturated NaHCO$_3$ solution (5 ml). The product was concentrated under vacuum then dissolved in MeCN/DMSO 1:1 and purified by MDAP. The desired fractions were combined and evaporated under vacuum to give the title compound (83 mg).

m/z (API-ES) 477 [M+H]$^+$

1H NMR (400 MHz, CHLOROFORM-d) δ ppm 3.11-3.18 (m, 2 H), 3.19-3.27 (m, 2 H), 3.82-3.90 (m, 2 H), 3.90-3.99 (m, 2 H), 7.32-7.38 (m, 1 H), 7.74-7.88 (m, 5 H), 7.92 (d, J=8.2 Hz, 2 H), 8.40 (dd, J=8.2, 2.3 Hz, 1 H), 8.75 (d, J=4.8 Hz, 1 H), 9.11-9.16 (m, 1 H).

Example 8

1-(4-Pyridinylcarbonyl)-4-{[4-(trifluoromethyl)phenyl]sulfonyl}piperazine

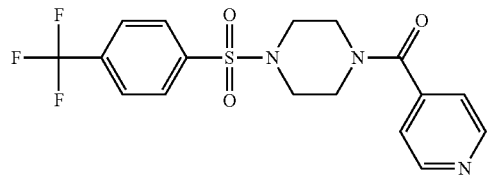 [SMILES: O=C(c1ccncc1)N1CCN(S(=O)(=O)c2ccc(C(F)(F)F)cc2)CC1]

To a solution of 1-{[4-(trifluoromethyl)phenyl]sulfonyl}piperazine (Description 1) (100 mg, 0.340 mmol) in DMF (5 ml) was added HOBT.H$_2$O (52.0 mg, 0.340 mmol), HBTU (129 mg, 0.340 mmol), 4-pyridinecarboxylic acid (41.8 mg, 0.340 mmol) and DIPEA (0.178 ml, 1.019 mmol. The reaction mixture was stirred for 2 hours at room temperature. Reaction mixture was transferred to a 100 ml round bottom flask and was reduced to dryness in vacuo. The residue was dissolved in DCM (50 ml) and was transferred to a separating funnel then washed with saturated NaHCO$_3$ solution (5 ml), twice. The organic layer was collected and dried with magnesium sulphate. The solid was removed by filtration and the filtrate collected in a 250 ml round bottom flask and reduced to dryness in vacuo. The residue was then dissolved in 1.8 ml 1:1 MeCN/DMSO and purified by MDAP in 2 batches. The fractions containing desired product were combined in a 250 ml round bottom flask and reduced in vacuo to yield the title compound (107 mg).

m/z (API-ES) 400 [M+H]$^+$

1H NMR (400 MHz, CHLOROFORM-d) δ ppm 2.87-3.31 (m, 4 H), 3.50 (br. s., 2 H), 3.90 (br. s., 2 H), 7.18-7.25 (m, 2 H), 7.82-7.93 (m, 4 H), 8.65-8.74 (m, 2 H).

Example 9

1-[(2-Methyl-4-pyridinyl)carbonyl]-4-{[4-(trifluoromethyl)phenyl]sulfonyl}piperazine

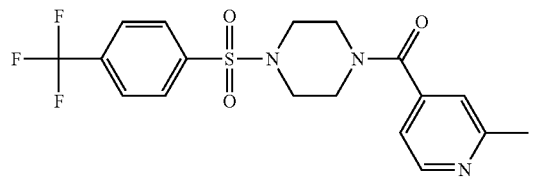 [SMILES: Cc1cc(C(=O)N2CCN(S(=O)(=O)c3ccc(C(F)(F)F)cc3)CC2)ccn1]

To a solution of 1-{[4-(trifluoromethyl)phenyl]sulfonyl}piperazine (Description 1) (100 mg, 0.340 mmol) in DMF (5 ml) was added HOBT.H₂O (52.0 mg, 0.340 mmol), HBTU (129 mg, 0.340 mmol), 2-methyl-4-pyridinecarboxylic acid (46.6 mg, 0.340 mmol) and DIPEA (0.178 ml, 1.02 mmol). The reaction mixture was stirred for 2 hours at room temperature. Reaction mixture was transferred to a 100 ml round bottom flask and was reduced to dryness in vacuo. The residue was dissolved in DCM (50 ml) and was transferred to a separating funnel then washed with saturated NaHCO₃ solution (5 ml), twice. The organic layer was collected and dried with magnesium sulphate. The solid was removed by filtration and the filtrate collected in a 250 ml round bottom flask and reduced to dryness in vacuo. The residue was then dissolved in 1.8 ml 1:1 MeCN/DMSO and purified by MDAP in 2 batches. The fractions containing desired product were combined in a 250 ml round bottom flask and reduced in vacuo to yield the title compound (81 mg).

m/z (API-ES) 414 [M+H]⁺

1H NMR (400 MHz, CHLOROFORM-d) δ ppm 2.59 (s, 3 H), 2.93-3.23 (m, 4 H), 3.50 (br. s., 2 H), 3.89 (br. s., 2 H), 7.01 (br. s., 1 H), 7.10 (s, 1 H), 7.80-7.95 (m, 4 H), 8.57 (d, J=5.0 Hz, 1 H).

Example 10

(2S)-2-methyl-1-[(2-methyl-4-pyridinyl)carbonyl]-4-{[4-(trifluoromethyl)phenyl]sulfonyl}piperazine formic acid salt (1:1)

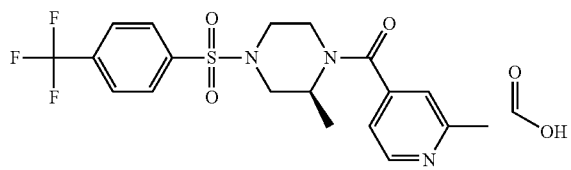

To a solution of (3S)-3-methyl-1-{[4-(trifluoromethyl)phenyl]sulfonyl}piperazine (Description 2) (80 mg, 0.259 mmol) in DMF (5 ml) was added 2-methyl-4-pyridinecarboxylic acid (35.6 mg, 0.259 mmol), HOBT.H₂O (39.7 mg, 0.259 mmol), HBTU (98 mg, 0.259 mmol) and DIPEA (0.136 ml, 0.778 mmol) and the reaction mixture was stirred at room temperature overnight. DMF was evaporated in vacuo then DCM (5 ml) was added and washed with saturated aq. NaHCO₃ solution (5 ml), dried on a phase separation cartridge and evaporated in vacuo. The crude material was dissolved in MeCN/DMSO 1:1 and purified by MDAP. The desired fractions were collected and concentrated in vacuo giving the title compound (74 mg).

m/z (API-ES) 428 [M+H]⁺

1H NMR (400 MHz, CHLOROFORM-d) (rotameric mixture) δ ppm 1.43 (d, J=6.6 Hz, 3 H), 2.41-2.58 (m, 2 H), 2.61 (s, 3 H), 3.17-3.53 (m, 2 H), 3.54-3.71 (m, 1 H), 3.71-4.01 (m, 1 H), 4.44-4.76 (m, 0.5 H), 4.86-5.14 (m, 0.5 H), 7.06 (d, J=5.1 Hz, 1 H), 7.13 (s, 1 H), 7.84 (d, J=8.5 Hz, 2 H), 7.88 (d, J=8.5 Hz, 2 H), 8.56 (d, J=5.1 Hz, 1 H).

Example 11

(2R)-4-[(4-chlorophenyl)sulfonyl]-2-methyl-1-(2-pyridinylcarbonyl)piperazine

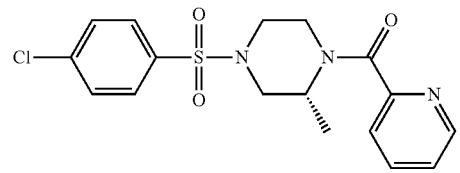 [SMILES: C[C@@H]1CN(S(=O)(=O)c2ccc(Cl)cc2)CCN1C(=O)c1ccccn1]

To a solution of (3R)-1-[(4-chlorophenyl)sulfonyl]-3-methylpiperazine (0.15 g, 0.55 mmol) in dry acetonitrile (5 mL) was added potassium carbonate (90 mg, 0.66 mmol) and 2-pyridinecarbonyl chloride (106 mg, 0.60 mmol) and the reaction mixture heated at 85° C. for 24 h. To the mixture was added ethyl acetate (30 mL) and the organic phase washed with 10% aqueous sodium bicarbonate (50 mL) before it was dried (MgSO₄), filtered and the solvent evaporated. The crude product was purified by Biotage SP4 (12+M silica column) eluting 0-4% MeOH in DCM to give the title compound as an off-white solid (95 mg).

m/z (API-ES) 380+382 (3:1) [M+H]⁺

Example 12

4-{[(3S)-3-methyl-4-(2-pyridinylcarbonyl)-1-piperazinyl]sulfonyl}benzonitrile

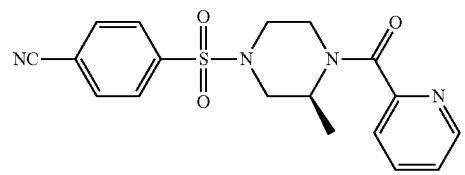 [SMILES: C[C@H]1CN(S(=O)(=O)c2ccc(C#N)cc2)CCN1C(=O)c1ccccn1]

To a solution of (2S)-2-methyl-1-(2-pyridinylcarbonyl)piperazine dihydrochloride (Description 16) (71 mg, 0.255 mmol) in DCM (3 ml) was added DIPEA (0.183 ml, 1.046 mmol) at room temperature and to it was slowly added 4-cyanobenzenesulfonyl chloride (56.6 mg, 0.281 mmol) and the resultant mixture then stirred for 3 h. 5 ml of water and 5 ml of DCM were added and the organic layer separated with a phase separation cartridge and then evaporated under vacuum. The crude material (120 mg) was purified via Biotage (12M silica column) using a gradient [i-hex/EtOAc] ([90/10] to [40/60]). The desired fractions were then collected and concentrated to dryness giving the title compound (48 mg) as a white solid.

m/z (API-ES) 371 [M+H]⁺

Examples 13 and 14

The compounds of Table 1 were prepared in a similar manner as the compound of Example 1 using the corresponding reactants.

TABLE 1

| Example no. | Name | Structure | m/z (API-ES) [M + H]+ |
|---|---|---|---|
| 13 | (2R)-2-methyl-4-[(3-methyl-2-pyridinyl)carbonyl]-1-{[4-(trifluoromethyl)phenyl]sulfonyl}piperazine | 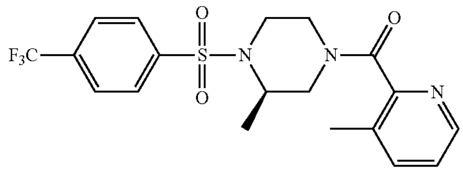 [SMILES: Cc1cccnc1C(=O)N1CCN(S(=O)(=O)c2ccc(C(F)(F)F)cc2)[C@H](C)C1] | 428 |
| 14 | (2S)-2-methyl-4-[(3-methyl-2-pyridinyl)carbonyl]-1-{[4-(trifluoromethyl)phenyl]sulfonyl}piperazine | 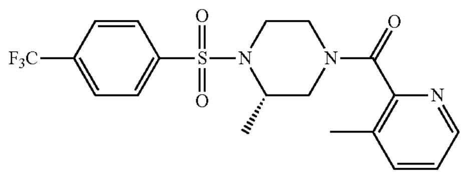 [SMILES: Cc1cccnc1C(=O)N1CCN(S(=O)(=O)c2ccc(C(F)(F)F)cc2)[C@@H](C)C1] | 428 |

Example 15

4-({(3S)-3-methyl-4-[(2-methyl-4-pyridinyl)carbonyl]-1-piperazinyl}sulfonyl)benzonitrile

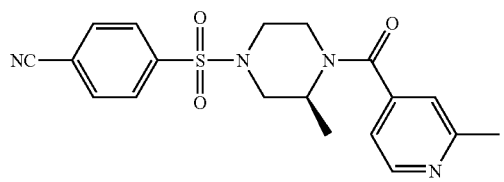 [SMILES: Cc1cc(C(=O)N2CCN(S(=O)(=O)c3ccc(C#N)cc3)C[C@@H]2C)ccn1]

The compound of Example 15 was prepared in a similar manner as the compound of Example 12 using the corresponding reactants.

m/z (API-ES) 385 [M+H]+

Example 16

1-[(4-Bromo-2-pyridinyl)carbonyl]-4-{[4-(trifluoromethyl)phenyl]sulfonyl}piperazine

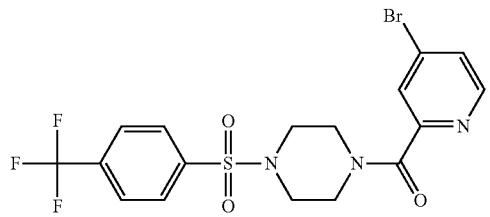 [SMILES: O=C(c1cc(Br)ccn1)N1CCN(S(=O)(=O)c2ccc(C(F)(F)F)cc2)CC1]

To a solution of 1-{[4-(trifluoromethyl)phenyl]sulfonyl}piperazine (Description 1) (200 mg, 0.680 mmol) in DMF (10 ml) was added 4-bromo-2-pyridinecarboxylic acid (137 mg, 0.680 mmol), HOBT.H₂O (104 mg, 0.680 mmol), HBTU (258 mg, 0.680 mmol) and DIPEA (0.356 ml, 2.039 mmol) and the reaction mixture was stirred at room temperature for 2.5 hours. The DMF was evaporated under vacuo then 10 ml of DCM were added and washed with 2M aq. HCl solution (10 ml) saturated aq. NaHCO₃ solution (10 ml) and brine (10 ml), dried on a phase separation cartridge and evaporated in vacuo. The crude material was purified by silica chromatography using a gradient isohexane/EtOAc [100/0] to [50/50] then to [0/100]). The desired fractions were then collected and concentrated to dryness to give the title compound (171 mg).

m/z (API-ES) 478,480 (1:1) [M+H]+

1H NMR (400 MHz, CHLOROFORM-d) δ ppm 3.10-3.16 (m, 2 H) 3.17-3.24 (m, 2 H) 3.76-3.85 (m, 2 H) 3.86-3.95 (m, 2 H) 7.54 (dd, J=5.3, 1.9 Hz, 1 H) 7.81-7.87 (m, 3 H) 7.88-7.94 (m, 2 H) 8.35 (d, J=5.3 Hz, 1 H).

Example 17

(2S)-1-[(4-Chloro-2-pyridinyl)carbonyl]-2-methyl-4-{[4-(trifluoromethyl)phenyl]sulfonyl}piperazine

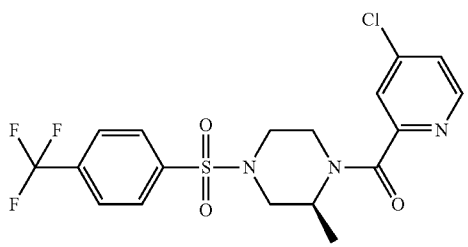 [SMILES: C[C@H]1CN(S(=O)(=O)c2ccc(C(F)(F)F)cc2)CCN1C(=O)c1cc(Cl)ccn1]

HATU (411 mg, 1.08 mmol) was added to a solution of 4-chloro-2-pyridinecarboxylic acid (142 mg, 0.90 mmol) in DMF (4 ml) and the mixture was treated with DIPEA (0.394 ml, 2.25 mmol). This mixture was stirred for ca. 10 min at ambient temperature. (3S)-3-Methyl-1-{[4-(trifluoromethyl)phenyl]sulfonyl}piperazine (Description 2) (333 mg, 1.082 mmol) was then added and stirring was continued for 1.5 h. The reaction mixture was partitioned between DCM and sat aq. NaHCO₃ solution (20 ml each). The layers were separated and the aqueous was washed with further DCM (2×20 ml). The combined organics were concentrated to leave a dark brown gum. Purification by silica chromatography (Biotage SP4, 25S cartridge), eluting with 12-100% ethyl acetate in isohexane, gave a pale yellow gum, shown to be impure by LCMS and NMR analysis. Further purification by MDAP gave the title compound as a colourless glass (159 mg).

m/z (API-ES) 448 [M+H]+

1H NMR (400 MHz, CHLOROFORM-d) (rotameric mixture) δ ppm 1.45 (d, J=9 Hz, 3 H), 2.38-2.52 (m, 1 H), 2.54-2.66 (m, 1 H), 3.24-3.37 (m, 0.5 H), 3.44-3.59 (m, 1 H), 3.63-3.77 (m, 1 H), 3.84-3.93 (m, 0.5 H), 3.98-4.08 (m, 0.5 H), 4.38-4.47 (m, 0.5 H), 4.56-4.65 (m, 0.5 H), 4.95-5.05 (m, 0.5 H), 7.36 (dd, J=5, 2 Hz, 1 H), 7.64 (br s, 1 H), 7.82 (d, J=8.5 Hz, 2 H), 7.88 (d, J=8.5 Hz, 2 H), 8.43 (d, J=5 Hz, 1H),

Example 18

N,N-Dimethyl-2-[((2S)-2-methyl-4-{[4-(trifluoromethyl)phenyl]sulfonyl}-1-piperazinyl)carbonyl]-4-pyridinamine hydrochloride

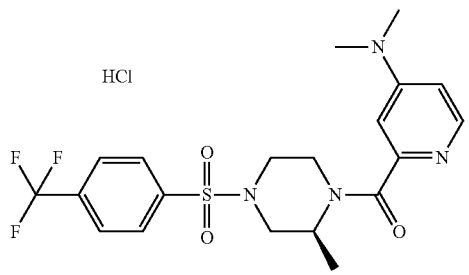 [SMILES: C[C@H]1CN(S(=O)(=O)c2ccc(C(F)(F)F)cc2)CCN1C(=O)c1cc(N(C)C)ccn1 ; Cl]

((2S)-1-[(4-Chloro-2-pyridinyl)carbonyl]-2-methyl-4-{[4-(trifluoromethyl)phenyl]sulfonyl}piperazine (48 mg, 0.11 mmol) (Example 17) was weighed into a microwave vial. Dimethylamine, 2M in methanol (1.6 ml, 3.20 mmol) was added, and the mixture was heated in the microwave to 120° C. for 12 h with stirring. The reaction mixture was concentrated to give the crude material as a yellow gum (59 mg). This was purified by MDAP (High pH system) to give the free base of the product as a colourless gum (41 mg).

m/z (API-ES) 457 [M+H]$^+$

1H NMR (400 MHz, CHLOROFORM-d) (rotameric mixture) δ ppm 1.34-1.48 (m, 3 H), 2.39-2.52 (m, 1 H), 2.62 (dd, J=11, 3.5 Hz, 1 H), 3.01 (s, 6 H), 3.21-3.32 (m, 0.5 H), 3.38-3.55 (m, 1 H), 3.62-3.73 (m, 1 H), 3.81-3.90 (m, 0.5 H), 4.01-4.11 (m, 0.5 H), 4.42-4.51 (m, 0.5 H), 4.53-4.62 (m, 0.5 H), 4.95-5.05 (m, 0.5 H), 6.46-6.51 (m, 1 H), 6.76 (br s, 1 H), 7.81 (d, J=8.5 Hz, 2 H), 7.87 (d, J=8.5 Hz, 2 H), 8.11 (d, J=6 Hz, 1 H), The material was dissolved in THF (0.5 ml) and treated with HCl in dioxan (4 M, 0.1 ml) and reconcentrated. The resulting colourless gum was triturated with ether, then dried, to give the title compound (47 mg) as a colourless solid.

m/z (API-ES) 457 [M+H]$^+$

Example 19

(2S)-1-{[4-(1-Azetidinyl)-2-pyridinyl]carbonyl}-2-methyl-4-{[4-(trifluoromethyl)phenyl]sulfonyl}piperazine

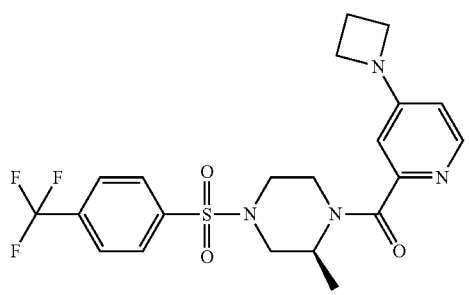 [SMILES: C[C@H]1CN(S(=O)(=O)c2ccc(C(F)(F)F)cc2)CCN1C(=O)c1cc(N2CCC2)ccn1]

((2S)-1-[(4-Chloro-2-pyridinyl)carbonyl]-2-methyl-4-{[4-(trifluoromethyl)phenyl]sulfonyl}piperazine (48 mg, 0.11 mmol) (Example 17) was transferred into a microwave vial as a solution in isopropanol (1.4 ml). Azetidine (0.144 ml, 2.14 mmol) was added, and the mixture was heated in the microwave to 120° C. for 12 h with stirring. The reaction mixture was concentrated to give the crude material as a colourless gum (167 mg). This was purified by MDAP (High pH system) to give the product as a pale yellow gum (41 mg). Trituration with diethylether gave the title compound as a pale yellow solid.

m/z (API-ES) 469 [M+H]$^+$

1H NMR (400 MHz, CHLOROFORM-d) (rotameric mixture) δ ppm 1.33-1.47 (m, 3 H), 2.38-2.51 (m, 3 H), 2.61 (dd, J=11.5, 3.5 Hz, 1 H), 3.19-3.30 (m, 0.5 H), 3.37-3.56 (m, 1 H), 3.60-3.73 (m, 1 H), 3.78-3.89 (m, 0.5 H), 3.90-4.07 (m, 4.5 H), 4.38-4.48 (m, 0.5 H), 4.51-4.60 (m, 0.5 H), 4.93-5.03 (m, 0.5 H), 6.21 (dd, J=5, 1.5 Hz, 1 H), 6.48 (br s, 1 H), 7.81 (d, J=8.5 Hz, 2 H), 7.87 (d, J=8.5 Hz, 2 H), 8.08 (d, J=6 Hz, 1 H), Equipment:

Mass-Directed Automated HPLC/Mass-Directed Automated Preparation (MDAP)

Where indicated in the above compounds, purification by mass-directed automated HPLC was carried out using the following apparatus and conditions:

Hardware

Waters 2525 Binary Gradient Module

Waters 515 Makeup Pump

Waters Pump Control Module

Waters 2767 Inject Collect

Waters Column Fluidics Manager

Waters 2996 Photodiode Array Detector

Waters ZQ Mass Spectrometer

Gilson 202 fraction collector

Gilson Aspec waste collector

Software

Waters MassLynx version 4 SP2

Column

The columns used are Waters Atlantis, the dimensions of which are 19 mm×100 mm (small scale) and 30 mm×100 mm (large scale). The stationary phase particle size is 5 µm.

Solvents

A: Aqueous solvent=Water+0.1% Formic Acid

B: Organic solvent=Acetonitrile+0.1% Formic Acid

Make up solvent=Methanol:Water 80:20

Needle rinse solvent=Methanol

Methods

There are five methods used depending on the analytical retention time of the compound of interest. They have a 13.5-minute runtime, which comprises of a 10-minute gradient followed by a 3.5 minute column flush and re-equilibration step.

Large/Small Scale 1.0-1.5=5-30% B

Large/Small Scale 1.5-2.2=15-55% B

Large/Small Scale 2.2-2.9=30-85% B

Large/Small Scale 2.9-3.6=50-99% B

Large/Small Scale 3.6-5.0=80-99% B (in 6 minutes followed by 7.5 minutes flush and re-equilibration)

Flow Rate

All of the above methods have a flow rate of either 20 mls/min (Small Scale) or 40 mls/min (Large Scale).

Liquid Chromatography/Mass Spectrometry

Analysis of the above compounds by Liquid Chromatography/Mass Spectrometry (LC/MS) was carried out using the following apparatus and conditions:

Hardware
Waters Acquity Binary Solvent Manager
Waters Acquity Sample Manager
Waters Acquity PDA
Waters ZQ Mass Spectrometer
Sedere Sedex 75
Software
Waters MassLynx version 4.1
Column The column used is a Waters Acquity BEH HPLC C18, the dimensions of which are 2.1 mm×50 mm. The stationary phase particle size is 1.7 μm.

Solvents
A: Aqueous solvent=Water+0.05% Formic Acid
B: Organic solvent=Acetonitrile+0.05% Formic Acid
Weak Wash=1:1 Methanol:Water
Strong Wash=Water
Method The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40° C.
The UV detection range is from 220 to 330 nm
Biotage SP4®

Biotage-SP4® is an automated purification system. It uses preloaded silica gel columns. The user applies their material to the top of the column and chooses solvents, gradients, flow rates, column size, collection method and eluting volumes.

Phase Separators (Hydrophobic Frit)

Phase separators are a range of ISOLUTE® columns fitted with an optimized frit material that easily separates aqueous phase from chlorinated solvents under gravity.

SCX—Strong Cation Exchange cartridge

Where indicated in the compounds, an SCX cartridge was used as part of the compound purification process. Typically an ISOLUTE SCX-2 cartridge was used. ISOLUTE SCX-2 is a silica-based sorbent with a chemically bonded propylsulfonic acid functional group.

ISOLUTE SCX-2 Chemical Data
Base Material: Silica, 50 μm
Functional Group Propylsulfonic acid
Capacity: 0.6 meq/g
Counter Ion: Proton
Pharmacological Data Compounds of the invention may be tested for in vitro biological activity in the hCa$_v$2.2 assay in accordance with the following studies:

Methods
Cell Biology

Stable cell lines expressing the human Ca$_v$2.2 α (α1$_B$) subunit, along with the human β3 and α2δ1 auxiliary subunits were created following sequential transfection and selection of human embryonic kidney (HEK293) cells. HEK293 cells were cultured in Dulbecco's modified Eagles media/F12 media (Invitrogen, Cat # 041-95750V) containing 10% foetal bovine serum, with added L-glutamine (2 mM; Invitrogen, Cat # 25030-024) and non-essential amino acids (5%; Invitrogen, Cat # 11140-035). Initially HEK293 cells were transfected with two plasmid vectors for expression of the hCa$_v$2.2 α subunit (pCIN5-hCa$_v$2.2 which carries a neomycin resistance marker) and the hCa$_v$ β3 subunit (pCIH-hCa$_v$ β3 which carries a hygromycin resistance marker). Clonal cell lines were isolated following selection in media supplemented with 0.4 mg ml$^{-1}$ Geneticin G418 (Invitrogen, Cat # 10131-027) and 0.1 mg ml$^{-1}$ hygromycin (Invitrogen, Cat # 10687-010). These clonal cell lines were assessed for Ca$_v$2.2 α/β3-mediated current expression using the IonWorks planar array electrophysiology technology (described below). A clonal line was identified that gave a reasonable level of functional Ca$_v$2.2 α/β3 current expression. This cell line was transfected with a plasmid vector for expression of the human α2δ1 subunit (pCIP-α2δ1 which carries a puromycin resistance marker) and clonal cell lines isolated following selection in media containing 0.62 μg ml$^{-1}$ puromycin (Sigma, Cat # P-7255), in addition to 0.4 mg ml$^{-1}$ Geneticin G418 and 0.1 mg ml$^{-1}$ hygromycin. Several cell lines were identified that gave robust levels of Ca$_v$2.2 α/β3/α2δ1-mediated current expression and one of these was selected for compound profiling. Expression of all three subunits within this cell line was continuously maintained by the inclusion of G418 (0.4 mg ml$^{-1}$), hygromycin (0.1 mg ml$^{-1}$) and puromycin (0.62 μg ml$^{-1}$). Cells were maintained at 37° C. in a humidified environment containing 5% CO$_2$ in air. Cells were liberated from the T175 culture flasks for passage and harvesting using TrpLE (Invitrogen, Cat # 12604-013).

Cell Preparation

Cells were grown to 30-60% confluence in T175 flasks and maintained at 30° C. for 24 hrs prior to recording. Cells were lifted by removing the growth media, washing with Ca$^{2+}$ free PBS (Invitrogen, Cat #14190-094) and incubating with 3 ml of warmed (37° C.) TrpLE (Invitrogen, Cat # 12604-013) for 6 minutes. Lifted cells were suspended in 10 ml of extracellular buffer. Cell suspension was then placed into a 15 ml tube and centrifuged for 2 minutes at 700 rpm. After centrifugation, the supernatant was removed and the cell pellet was resuspended in 4.5 ml of extracellular solution.

Electrophysiology

Currents were recorded at room temperature (21-23° C.) using the IonWorks planar array electrophysiology technology (Molecular Devices Corp.). Stimulation protocols and data acquisition were carried out using a microcomputer (Dell Pentium 4). In order to determine planar electrode hole resistances (Rp), a 10 mV, 160 ms potential difference was applied across each hole. These measurements were performed before cell addition. After cell addition a seal test was performed prior to antibiotic (amphotericin) circulation to achieve intracellular access. Leak subtraction was conducted in all experiments by applying a 160 ms hyperpolarizing (10 mV) prepulse 200 ms before the test pulses to measure leak conductance. Test pulses stepping from the holding potential ($V_H$) of −90 mV to +10 mV were applied for 20 ms and repeated 10 times at a frequency of 10 Hz. In all experiments, the test pulse protocol was performed in the absence (pre-read) and presence (post-read) of a compound. Pre- and post-reads were separated by a compound addition followed by a 3-3.5 min incubation.

Solutions and Drugs

The intracellular solution contained the following (in mM): K-gluconate 120, KCl 20 mM, MgCl$_2$ 5, EGTA 5, HEPES 10, adjusted to pH 7.3. Amphotericin was prepared as 30 mg/ml stock solution and diluted to a final working concentration of 0.2 mg ml$^{-1}$ in intracellular buffer solution. The extracellular solution contained the following (in mM): Na-gluconate 120, NaCl 20, MgCl$_2$ 1, HEPES 10, BaCl$_2$ 5, adjusted to pH 7.4.

Compounds were prepared in DMSO as 10 mM stock solutions and subsequent 1:3 serial dilutions performed. Finally the compounds were diluted 1:100 in external solution resulting in a final DMSO concentration of 1%.

Data Analysis

The recordings were analysed and filtered using seal resistance (>40 MΩ), resistance reduction (>35%) and peak current amplitude (>200 pA) in the absence of compound to eliminate unsuitable cells from further analysis. Paired comparisons between pre-compound and post-compound additions were used to determine the inhibitory effect of each compound. The concentrations of compounds required to inhibit current elicited by the $1^{st}$ depolarising pulse by 50% (tonic pIC50) were determined by fitting of the Hill equation to the concentration response data. In addition the use-dependent inhibitory properties of the compounds were determined by assessing the effect of compounds on the $10^{th}$ versus $1^{st}$ depolarising pulse. The ratio of the $10^{th}$ over $1^{st}$ pulse was determined in the absence and presence of drug and the % use-dependent inhibition calculated. The data was fitted using the same equation as for the tonic $pIC_{50}$ and the concentration producing 30% inhibition (use-dependent $pUD_{30}$) determined.

The compounds of Examples 1 to 15 and 17 to 19 were tested in the $hCa_v2.2$ assay and demonstrated the following $pUD_{30}$ and $pIC_{50}$ values. Compounds were tested in the form as described in the Examples. All compounds tested have been tested one or more times (up to 6 times). Variations in $pUD_{30}$ and $pIC_{50}$ values may arise between tests.

The compounds 1 to 11, 13, 14, 17 to 19 exhibited a $pUD_{30}$ value of 4.5 or more than 4.5. The compounds 1, 2, 4 to 7, 9, 10, 14, 17 to 19 exhibited a $pUD_{30}$ value of 5.0 or more than 5.0. The compounds 2, 5, 7, 17 and 19 exhibited a $pUD_{30}$ value of 5.5 or more than 5.5.

The compounds 1 to 15 and 17 to 19 exhibited a mean $pIC_{50}$ value of 5.0 or less than 5.0. The compounds 1 to 15 exhibited a mean $pIC_{50}$ value of 4.5 or less than 4.5.

The invention claimed is:

1. A compound of formula (I), or a pharmaceutically acceptable salt thereof, for use in therapy, wherein:

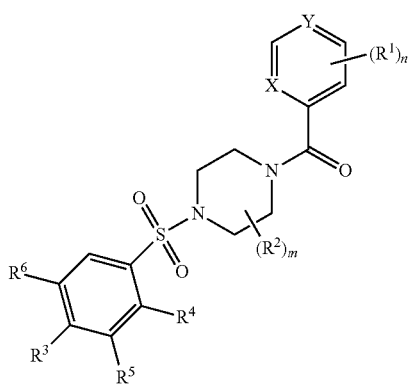

(I)

X is nitrogen and Y is carbon, or
X is carbon and Y is nitrogen;
m is 1;
n is 0, 1, or 2;
where present, each $R^1$ is independently selected from $C_{1-4}$ alkyl, $C_{1-4}$ alkoxy, $C_{3-6}$ cycloalkyl, cyano, $NR^{1a}R^{1b}$, and halogen;
$R^{1a}$ and $R^{1b}$ are independently selected from hydrogen, $C_{1-4}$ alkyl, $C_{3-6}$ cycloalkyl, and a 4 to 6 membered heterocyclyl;
or $R^{1a}$ and $R^{1b}$ together with the nitrogen atom to which they are attached form a 4 to 6 membered heterocyclic ring;
$R^2$ is methyl;
$R^3$ is hydrogen, halogen, cyano, $C_{1-4}$ haloalkyl, or $C_{1-4}$ haloalkoxy;
$R^4$ is hydrogen or $C_{1-4}$ alkyl;
$R^5$ is hydrogen, halogen, cyano, $C_{1-4}$ haloalkyl, or $C_{1-4}$ haloalkoxy;
$R^6$ is hydrogen, halogen, cyano, $C_{1-4}$ haloalkyl, or $C_{1-4}$ haloalkoxy;
such that at least 1 of $R^3$, $R^4$, $R^5$, and $R^6$ is a group other than hydrogen.

2. The compound, or a pharmaceutically acceptable salt thereof, according to claim 1, wherein $R^1$ is selected from $C_{1-4}$ alkyl, $C_{1-4}$ alkoxy, cyano, and $NR^{1a}R^{1b}$.

3. The compound, or a pharmaceutically acceptable salt thereof, according to claim 2, wherein $R^1$ is selected from $C_{1-4}$ alkyl and $C_{1-4}$ alkoxy.

4. The compound, or a pharmaceutically acceptable salt thereof, according to claim 3, wherein $R^1$ is selected from methyl and methoxy.

5. The compound, or a pharmaceutically acceptable salt thereof, according to claim 4, wherein $R^1$ is methyl.

6. The compound, or a pharmaceutically acceptable salt thereof, according to claim 1, wherein $R^1$ is $NR^{1a}R^{1b}$ and $R^{1a}$ and $R^{1b}$ are independently selected from hydrogen and $C_{1-4}$ alkyl, or $R^{1a}$ and $R^{1b}$ together with the nitrogen atom to which they are attached form a 4 to 6 membered heterocyclic ring.

7. The compound, or a pharmaceutically acceptable salt thereof, according to claim 6, wherein $R^{1a}$ and $R^{1b}$ are $C_{1-4}$ alkyl, or $R^{1a}$ and $R^{1b}$ together with the nitrogen atom to which they are attached form a 4 or 5 membered heterocyclic ring.

8. The compound, or a pharmaceutically acceptable salt thereof, according to claim 7, wherein $R^{1a}$ and $R^{1b}$ are $C_{1-4}$ alkyl, or $R^{1a}$ and $R^{1b}$ together with the nitrogen atom to which they are attached form a morpholinyl, pyrrolidinyl, or azetidinyl ring.

9. The compound, or a pharmaceutically acceptable salt thereof, according to claim 8, wherein $R^{1a}$ and $R^{1b}$ are $C_{1-4}$ alkyl.

10. The compound, or a pharmaceutically acceptable salt thereof, according to claim 9, wherein $R^{1a}$ and $R^{1b}$ are selected from methyl and ethyl.

11. The compound, or a pharmaceutically acceptable salt thereof, according to claim 1, wherein n is 0 or 1.

12. The compound, or a pharmaceutically acceptable salt thereof, according to claim 11, wherein n is 1.

13. The compound, or a pharmaceutically acceptable salt thereof, according to claim 1, wherein $R^2$ is methyl.

14. The compound, or a pharmaceutically acceptable salt thereof, according to claim 13, wherein $R^2$ is methyl and m is 1.

15. The compound, or a pharmaceutically acceptable salt thereof, according to claim 14, wherein the compound is a compound of formula (Ia)

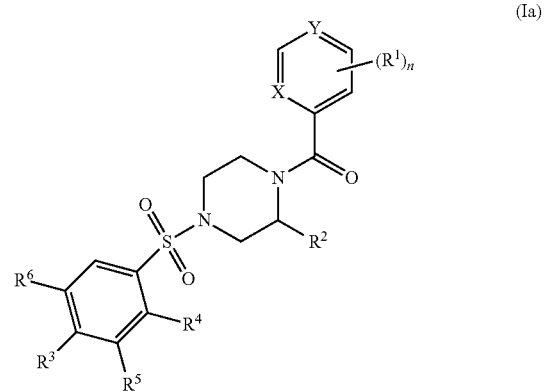

(Ia)

or a pharmaceutically acceptable salt thereof.

16. The compound, or a pharmaceutically acceptable salt thereof, according to claim 15, wherein the compound is a compound of formula (Ib)

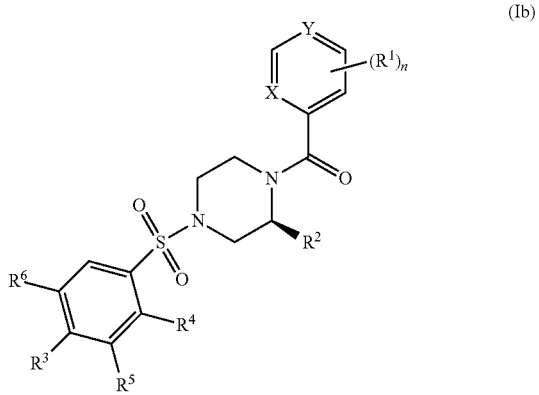

or a pharmaceutically acceptable salt thereof.

17. The compound, or a pharmaceutically acceptable salt thereof, according to claim 1, wherein $R^3$ is $C_{1-4}$ haloalkyl, or $C_{1-4}$ haloalkoxy.

18. The compound, or a pharmaceutically acceptable salt thereof, according to claim 17, wherein $R^3$ is trifluoromethyl, trifluoromethoxy, or difluoromethoxy.

19. The compound, or a pharmaceutically acceptable salt thereof, according to claim 1, wherein $R^4$ is hydrogen or methyl.

20. The compound, or a pharmaceutically acceptable salt thereof, according to claim 19, wherein $R^4$ is hydrogen.

21. The compound, or a pharmaceutically acceptable salt thereof, according to claim 1, wherein $R^5$ and $R^6$ are independently selected from hydrogen and $C_{1-4}$ haloalkyl.

22. The compound, or a pharmaceutically acceptable salt thereof, according to claim 21, wherein $R^5$ and $R^6$ are independently selected from hydrogen and trifluoromethyl.

23. The compound, or a pharmaceutically acceptable salt thereof, according to claim 22, wherein each of $R^5$ and $R^6$ is hydrogen.

24. A method for the treatment of pain in a human in need thereof comprising administering to said human a therapeutically effective amount of a compound, or a pharmaceutically acceptable salt thereof, according to claim 1.

25. A pharmaceutical composition comprising:
(a) a compound, or a pharmaceutically acceptable salt thereof, according to claim 1; and
(b) a pharmaceutically acceptable excipient.

* * * * *